(12) United States Patent
Bonde et al.

(10) Patent No.: US 10,328,271 B2
(45) Date of Patent: Jun. 25, 2019

(54) IMPLANTABLE ELECTRICAL STIMULATOR WITH DEFLECTING TIP LEAD

(71) Applicant: Medtronic, Inc., Minneapolis, MN (US)

(72) Inventors: Eric H. Bonde, Minnetonka, MN (US); John E. Kast, Hugo, MN (US); Erik R. Scott, Maple Grove, MN (US); Xuan K. Wei, Minnetonka, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 143 days.

(21) Appl. No.: 15/334,627

(22) Filed: Oct. 26, 2016

(65) Prior Publication Data

US 2017/0136244 A1 May 18, 2017

Related U.S. Application Data

(60) Provisional application No. 62/254,516, filed on Nov. 12, 2015.

(51) Int. Cl.
*A61N 1/375* (2006.01)
*A61N 1/05* (2006.01)
*A61N 1/36* (2006.01)
*A61N 1/378* (2006.01)

(52) U.S. Cl.
CPC ........... *A61N 1/375* (2013.01); *A61N 1/0551* (2013.01); *A61N 1/3605* (2013.01); *A61N 1/3787* (2013.01)

(58) Field of Classification Search
CPC .... A61N 1/0551; A61N 1/3605; A61N 1/372; A61N 1/375; A61N 1/3752
See application file for complete search history.

(56) References Cited

U.S. PATENT DOCUMENTS

| | | | |
|---|---|---|---|
| 2,717,600 | A | 9/1955 | Huber |
| 4,136,703 | A | 1/1979 | Wittkampf |
| 4,141,365 | A | 2/1979 | Fischell et al. |
| 4,512,351 | A | 4/1985 | Pohndorf |
| 4,630,611 | A | 12/1986 | King |

(Continued)

FOREIGN PATENT DOCUMENTS

| | | |
|---|---|---|
| DE | 202004017861 | 2/2005 |
| EP | 0832667 A2 | 4/1998 |

(Continued)

OTHER PUBLICATIONS

"Destino Twist, Deflectable Steerable Guiding Sheath," Oscor, Aug. 2014, 2 pp.

(Continued)

*Primary Examiner* — Allen Porter
(74) *Attorney, Agent, or Firm* — Patterson Thuente Pedersen, P.A.

(57) ABSTRACT

In some examples, an implantable medical device includes an implantable housing, a neurostimulator within the housing, a plurality of electrodes, an implantable lead coupled to the housing, and an actuator formed with the housing. The implantable lead includes at least one electrode of the plurality of electrodes and one or more conductors coupling the at least one electrode to the neurostimulator. The actuator is configured to cause at least a portion of the implantable lead to deflect.

28 Claims, 22 Drawing Sheets

(56) References Cited

U.S. PATENT DOCUMENTS

| | | |
|---|---|---|
| 4,676,249 A | 6/1987 | Arenas et al. |
| 4,808,157 A | 2/1989 | Coombs |
| 4,815,478 A | 3/1989 | Buchbinder et al. |
| 4,922,910 A | 5/1990 | Kanai et al. |
| 4,940,062 A | 7/1990 | Hampton et al. |
| 4,961,434 A | 10/1990 | Stypulkowski |
| 5,000,194 A | 3/1991 | van den Honert et al. |
| 5,040,543 A | 8/1991 | Badera et al. |
| 5,152,749 A | 10/1992 | Giesy et al. |
| 5,170,787 A | 12/1992 | Lindegren |
| 5,255,691 A | 10/1993 | Otten |
| 5,327,906 A | 7/1994 | Fideler |
| 5,391,199 A | 2/1995 | Ben-Haim |
| 5,423,877 A | 6/1995 | Mackey |
| 5,443,492 A | 8/1995 | Stokes et al. |
| 5,522,874 A | 6/1996 | Gates |
| 5,562,695 A | 10/1996 | Obenchain |
| 5,649,970 A | 7/1997 | Loeb et al. |
| 5,662,119 A | 9/1997 | Brennen et al. |
| 5,669,882 A | 9/1997 | Pyles |
| 5,728,148 A | 3/1998 | Bostrom et al. |
| 5,800,465 A | 9/1998 | Thompson et al. |
| 5,824,031 A | 10/1998 | Cookston et al. |
| 5,830,188 A | 11/1998 | Abouleish |
| 5,843,148 A | 12/1998 | Gijsbers et al. |
| 5,899,909 A | 5/1999 | Claren et al. |
| 6,038,480 A | 3/2000 | Hrdlicka et al. |
| 6,059,739 A | 5/2000 | Baumann |
| 6,104,957 A | 8/2000 | Alo et al. |
| 6,238,389 B1 | 5/2001 | Paddock et al. |
| 6,249,707 B1 | 6/2001 | Kohnen et al. |
| 6,360,750 B1 | 3/2002 | Gerber et al. |
| 6,473,653 B1 | 10/2002 | Schallhorn et al. |
| 6,493,590 B1 | 12/2002 | Wessman et al. |
| 6,510,347 B2 | 1/2003 | Borkan |
| 6,553,264 B2 | 4/2003 | Redko et al. |
| 6,587,733 B1 | 7/2003 | Cross, Jr. et al. |
| 6,592,573 B2 | 7/2003 | Castaneda et al. |
| 6,607,496 B1 | 8/2003 | Poor et al. |
| 6,733,500 B2 | 5/2004 | Kelley et al. |
| 6,757,970 B1 | 7/2004 | Kuzma et al. |
| 6,805,675 B1 | 10/2004 | Gardeski et al. |
| 6,836,687 B2 | 12/2004 | Kelley et al. |
| 6,847,849 B2 | 1/2005 | Mamo et al. |
| 6,971,393 B1 | 12/2005 | Mamo et al. |
| 6,999,819 B2 | 2/2006 | Swoyer et al. |
| 7,056,314 B1 | 6/2006 | Florio et al. |
| 7,220,242 B2 | 5/2007 | Putter et al. |
| 7,328,071 B1 | 2/2008 | Stehr et al. |
| 7,544,197 B2 | 6/2009 | Kelsch et al. |
| 7,668,601 B2 | 2/2010 | Hegland et al. |
| 7,763,034 B2 | 7/2010 | Siegel et al. |
| 8,954,162 B2 | 2/2015 | Bonde et al. |
| 9,399,130 B2 | 7/2016 | Bonde et al. |
| 2002/0147485 A1 | 10/2002 | Mamo et al. |
| 2002/0183817 A1 | 12/2002 | Van Venrooij et al. |
| 2003/0028147 A1 | 2/2003 | Aves et al. |
| 2003/0045919 A1 | 3/2003 | Swoyer et al. |
| 2003/0083724 A1 | 5/2003 | Jog et al. |
| 2003/0171644 A1 | 9/2003 | Anderson et al. |
| 2003/0176875 A1 | 9/2003 | Anderson et al. |
| 2003/0212305 A1 | 11/2003 | Anderson et al. |
| 2003/0236557 A1 | 12/2003 | Whitehurst et al. |
| 2004/0015204 A1 | 1/2004 | Whitehurst et al. |
| 2004/0015205 A1 | 1/2004 | Whitehurst et al. |
| 2004/0059280 A1 | 3/2004 | Makower et al. |
| 2004/0098074 A1 | 5/2004 | Erickson et al. |
| 2004/0138527 A1 | 7/2004 | Bonner et al. |
| 2004/0138675 A1 | 7/2004 | Crabtree |
| 2004/0193228 A1 | 9/2004 | Gerber |
| 2004/0210245 A1 | 10/2004 | Erickson et al. |
| 2005/0033372 A1 | 2/2005 | Gerber |
| 2005/0055063 A1 | 3/2005 | Loeb et al. |
| 2005/0090728 A1 | 4/2005 | Mest |
| 2005/0096667 A1 | 5/2005 | Smith et al. |
| 2005/0234507 A1 | 10/2005 | Geske et al. |
| 2005/0240238 A1 | 10/2005 | Mamo et al. |
| 2005/0267555 A1 | 12/2005 | Marnfeldt et al. |
| 2006/0058588 A1 | 3/2006 | Zdeblick |
| 2006/0089633 A1 | 4/2006 | Bleich et al. |
| 2006/0095079 A1 | 5/2006 | Gerber |
| 2006/0129101 A1 | 6/2006 | McGuckin, Jr. |
| 2006/0168805 A1 | 8/2006 | Hegland et al. |
| 2006/0173262 A1 | 8/2006 | Hegland et al. |
| 2007/0027515 A1 | 2/2007 | Gerber |
| 2007/0173900 A1 | 7/2007 | Siegel et al. |
| 2008/0200769 A1 | 8/2008 | Sharma et al. |
| 2008/0269716 A1 | 10/2008 | Bonde et al. |
| 2008/0269763 A1 | 10/2008 | Bonde et al. |
| 2009/0192381 A1 | 7/2009 | Brockway et al. |
| 2010/0292769 A1* | 11/2010 | Brounstein ......... A61N 1/0551 607/117 |
| 2011/0106100 A1 | 5/2011 | Bischoff |
| 2011/0257709 A1 | 10/2011 | Ackermann et al. |
| 2011/0257710 A1 | 10/2011 | Ackermann et al. |
| 2013/0110201 A1 | 5/2013 | Bonde et al. |
| 2013/0274843 A1 | 10/2013 | Barker et al. |
| 2013/0317588 A1 | 11/2013 | Howard et al. |
| 2014/0172034 A1 | 6/2014 | Bornzin et al. |
| 2016/0310751 A1 | 10/2016 | Bonde et al. |

FOREIGN PATENT DOCUMENTS

| | | |
|---|---|---|
| EP | 0922466 A2 | 6/1999 |
| EP | 1048270 A1 | 11/2000 |
| EP | 1048271 A2 | 11/2000 |
| EP | 1342454 A1 | 9/2003 |
| EP | 0832667 B1 | 2/2004 |
| FR | 2688407 A1 | 9/1993 |
| WO | 02068042 A1 | 9/2002 |
| WO | 2003084398 A1 | 10/2003 |
| WO | 2005009531 A1 | 2/2005 |
| WO | 2005032650 A1 | 4/2005 |
| WO | 2005118057 A2 | 12/2005 |
| WO | 2006133444 A2 | 12/2006 |
| WO | 2006133445 A2 | 12/2006 |

OTHER PUBLICATIONS

Abrams et al., "The role of neuromodulation in the management of urinary urge incontinence," British Journal of Urology International, vol. 91, No. 4, Mar. 2003, pp. 355-359.

Ishigooka et al., "A new technique for sacral nerve stimulation: a percutaneous method for urinary incontinence caused by spinal cord injury," British Journal of Urology, vol. 81, No. 2, Feb. 1998, pp. 315-318.

Spinelli et al., "New Percutaneous Technique of Sacral Nerve Stimulation Has High Initial Success Rate: Preliminary Results," European Urology, vol. 43, No. 1, Jan. 2003, pp. 70-74.

Zhang et al., "The Permeability Characteristics of Silicone Rubber," Society for the Advancement of Material and Process Engineering, Nov. 6-9, 2006, 10 pp.

International Search Report and Written Opinion from International Application No. PCT/US2016/060073, dated Feb. 27, 2017, 9 pp.

* cited by examiner

IMPLANTABLE ELECTRICAL STIMULATOR WITH DEFLECTING TIP LEAD

This application claims the benefit of U.S. Provisional Application No. 62/254,516, filed Nov. 12, 2015, the entire content of which is incorporated by reference herein in its entirety.

TECHNICAL FIELD

The disclosure relates to medical devices and, more particularly, implantable electrical stimulators with leads carrying electrodes.

BACKGROUND

Implantable medical devices may be configured to deliver electrical stimulation therapy and/or monitor physiological signals. Electrical stimulation of nerve tissue, for example, may provide relief for a variety of disorders, improving the quality of life for many patients.

Some implantable medical devices may employ elongated electrical leads that carry electrodes. For example, electrodes may be located at a distal portion of a lead. A proximal portion of the lead may include electrical contacts that are coupled to the electrodes via conductors within the lead and coupled to terminals in an implantable medical device housing, which may contain electronic circuitry such as electrical stimulation generation circuitry and/or sensing circuitry.

Electrical stimulation may be delivered for spinal cord stimulation (SCS), peripheral nerve stimulation (PNS), peripheral nerve field stimulation (PNFS), deep brain stimulation (DBS), cortical stimulation (CS), pelvic floor stimulation, gastric stimulation, and the like.

SUMMARY

The disclosure is directed to a method for implanting a lead of an implantable medical device with a deflecting tip adjacent to a nerve of a patient. The disclosure is also directed to an implantable medical device comprising a combination of an electrical stimulator, a lead with a deflecting tip, and an actuator configured to cause the tip to deflect.

In one example, the disclosure is directed to an implantable medical device including an implantable housing, a neurostimulator within the housing, a plurality of electrodes, an implantable lead coupled to the housing, and an actuator formed with the housing. The implantable lead may include at least one electrode of the plurality of electrodes and one or more conductors coupling the at least one electrode to the neurostimulator. The actuator may be configured to cause at least a portion of the implantable lead to deflect.

In another example, the disclosure is directed to a method of positioning an implantable medical device within a patient. The implantable medical device may include an implantable housing, a neurostimulator within the housing, a plurality of electrodes, and an implantable lead coupled to the housing. The implantable lead may include at least one electrode of the plurality of electrodes and one or more conductors coupling the at least one electrode to the neurostimulator. The method may include deflecting at least a portion of the implantable lead in response to movement of an actuator formed within the housing.

In yet another example, the disclosure is directed to an implantable medical device including an implantable housing, a neurostimulator within the housing, a plurality of electrodes, an implantable lead coupled to the housing, and a means, formed within the housing, for causing at least a portion of the implantable lead to deflect. The implantable lead may include at least one electrode of the plurality of electrodes and one or more conductors coupling the at least one electrode to the neurostimulator.

The details of one or more examples of the invention are set forth in the accompanying drawings and the description below. Other features, objects, and advantages of the invention will be apparent from the description and drawings, and from the claims.

DETAILED DESCRIPTION

Figure 1:
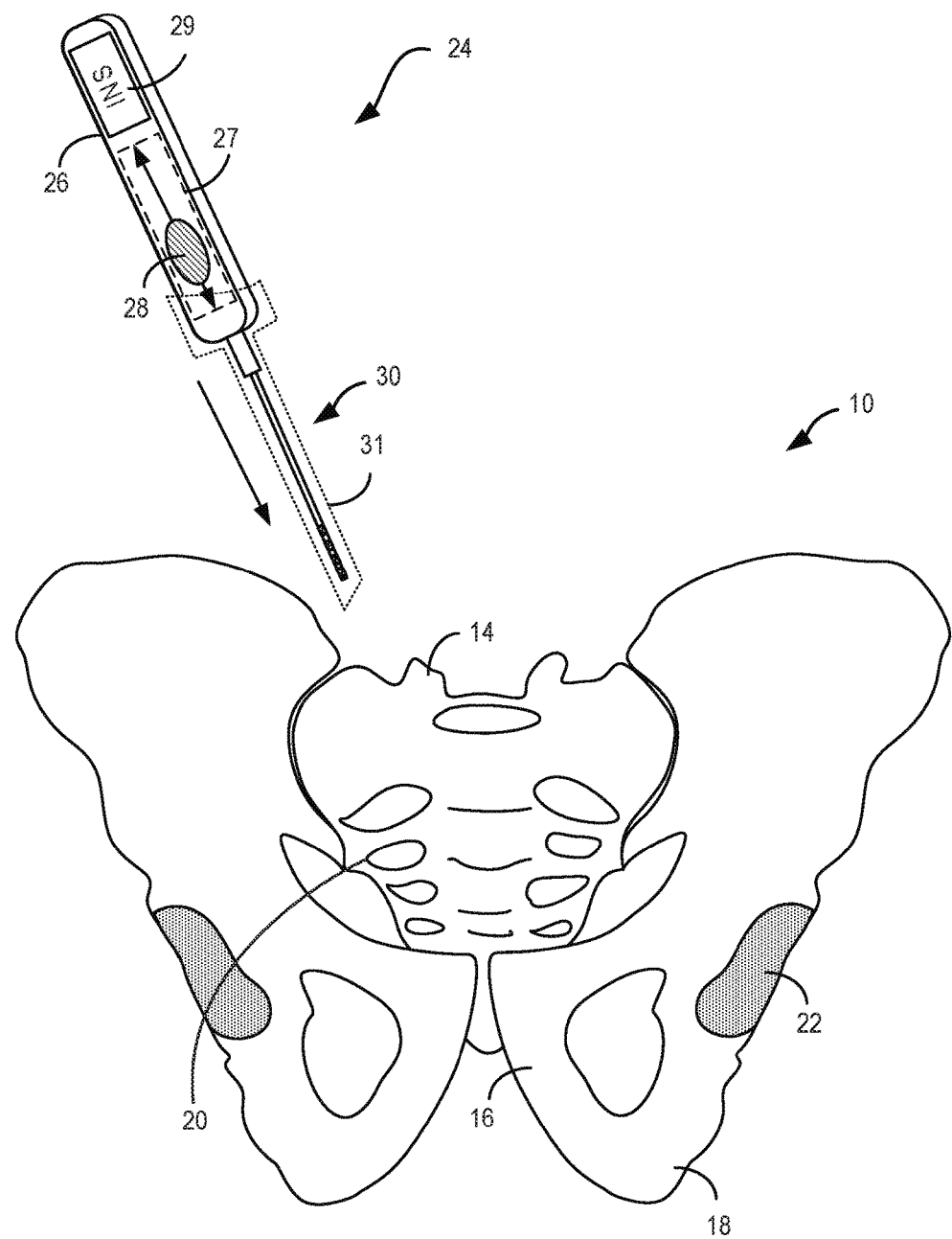
FIG. 1 is a schematic diagram illustrating an exemplary implantable medical device (IMD), having an implantable neural electrical stimulator (INS), a lead with a deflecting tip, and an actuator for causing the tip of lead 30 to deflect, and a method of inserting the deflecting tip of the lead adjacent a nerve site of the patient.

FIG. 1 is a schematic diagram illustrating an exemplary implantable medical device (IMD) 24 having an implantable neural electrical stimulator (INS) 29, a lead 30 with a deflecting tip, and an actuator 28 for causing the tip of lead 30 to deflect.

FIG. 1 also illustrates a method of inserting the deflecting tip of lead 30 adjacent a nerve site of the patient. In the example of FIG. 1, the deflecting tip of lead 30 is inserted through a sacral foramen 20 of the pelvis 10 of a human patient, e.g., for sacral nerve stimulation. Lead 30 may comprise one or more electrodes arranged for unipolar, bipolar, or multipolar stimulation. In the example of a unipolar lead with one or more electrodes, a second one or more electrodes may be housed in housing 26. IMD 24 of FIG. 1 represents an example of an IMD comprising an implantable housing, a neurostimulator within the housing, a plurality of electrodes, an implantable lead coupled to the housing and comprising at least one electrode of the plurality of electrodes and one or more conductors coupling the at least one electrode to the neurostimulator, and an actuator formed in the housing and configured to cause at least a portion of the implantable lead to deflect.

Urinary incontinence, fecal incontinence, sexual dysfunction, pelvic pain and other pelvic floor disorders are common problems afflicting people of all ages, genders, and races. Many of the disorders may be associated with aging, injury, or illness. In some cases, pelvic floor disorders can be attributed to improper nerve function. For example, aging can often result in nerve disorders that prevent proper operation of the bladder, sphincter muscles, or sexual organs. Nerves, such as the sacral nerve, pudendal nerve, or branches of the pudendal nerve, running though the pelvic floor regulate urinary and sexual function. Urinary incontinence or sexual dysfunction can arise when there is breakdown in communication within the nervous system.

Electrical stimulation of nerves in the pelvic floor may provide an effective therapy for a variety of disorders. For example, a surgeon may implant an electrical stimulation lead adjacent to the sacral nerve, pudendal nerve, or branches of the pudendal nerve. An implantable electrical stimulator, sometimes referred to as a neurostimulator, may be provided to deliver electrical stimulation through the lead. In the case of urinary incontinence, as an example, the stimulation may induce urinary sphincter constriction or reduce bladder wall constriction to aid the patient in reducing unwanted urinary voiding. Also, the stimulation may be effective in restoring sexual function or alleviating pelvic floor pain. As another example, the stimulation may be effective in reducing pelvic pain. Stimulation leads are ordinarily implanted surgically or percutaneously.

A physician may deflect the tip of the lead to place the lead at the target nerve site and perform test stimulation to confirm an effective stimulation location. After placing the lead at the target nerve site, the introducer may be removed and the lead along with the implantable medical device may be implanted by the physician. This placement and implantation method may provide an easier and more consistent procedure than a placement procedure that requires an implant tool.

Electrical stimulation of the sacral nerve may provide therapy for patients experiencing urinary incontinence, urinary retention, bowel disorders such as fecal incontinence, constipation, sexual dysfunction, or other pelvic floor disorders related to pelvic nerve function. The procedure described herein may also be directed to the implantation of electrical leads adjacent to other sacral nerves or other nerves near the sacrum. For example, the nerve of the clitoris may be accessed and stimulated to treat sexual dysfunction. In addition, the procedure may be applied to female or male patients. The IMD may also be used for stimulation in other areas of the body, according to particular needs. For example, an IMD having a lead with a deflecting tip, as described in this disclosure, may be used for various types of stimulation, such as spinal cord stimulation (SCS), peripheral nerve stimulation (PNS), peripheral nerve field stimulation (PNFS), deep brain stimulation (DBS), cortical stimulation (CS), gastric stimulation, and the like. As one example, the deflecting tip of the device described herein may be used to better access anatomy of the heart including, for example, the left ventricle of the heart.

In various examples, an IMD formed in accordance with this disclosure may provide one or more advantages. For example, the IMD may provide an easier and more consistent procedure for implanting the stimulation lead near a nerve, such as the sacral nerve in pelvic floor applications. The IMD may also reduce the risk of nerve tissue damage associated with other lead implantation procedures. In addition, an improved IMD may not only decrease the time and cost associated with lead implantation, but increase the number of patients who may utilize sacral nerve or other pelvic floor nerve stimulation to treat a variety of conditions. Further, implantation may utilize established skills of the physician. Additional advantages may include more secure placement of a lead. In some cases, external imaging techniques such as fluoroscopy may be unnecessary to achieve proper lead placement.

Combining an INS, a lead configured to deflect, and an actuator for deflecting the lead into a single, implantable device may allow for a simple and efficient implant procedure and ongoing therapy. For example, combining the elements into a single, implantable device may reduce the number of steps, amount of time, and number of tools used for the implant procedure, while still allowing for satisfactory placement of the lead adjacent to a target nerve site. The device may eliminate the need for tunneling, pocket creation, and implantation of an IPG. The simplified implant device using the combined system may allow for a procedure using only local anesthesia, reduced bleeding, and an office-based procedure. The device may eliminate the need for an open port during trial use to allow for a smooth transition from trial use to chronic use without additional surgery and to allow for more predictable chronic results based on trial results. In some examples, the device may be externally powered at a patient's convenience and according to therapy needs to allow for more convenient and effective therapy and improved outcomes.

Additionally, reliability may be improved by, for example, reducing the chance of faulty electrical connection between the lead and the INS. For example, using conventional systems including a lead that must be implanted before connection to an INS, a physician may need to properly insert the lead and then maintain alignment of the lead while simultaneously electrically connecting it to the INS by, for example, connecting connectors of the lead and the INS using a mechanical lock such as a set screw. This process may be susceptible to errors including misaligned or unaligned electrical connectors or crushed connector rings. Combining the elements into a single, implantable device eliminates the need for the physician to electrically connect the lead to the INS and may thus reduce the chance of faulty connections and improve reliability.

As shown in FIG. 1, an anterior view of pelvis 10 includes sacrum 14, inferior pubic ramus 16, ischial tuberosity 18, sacral foramen 20, and acetabulum 22. IMD 24 includes housing 26, an actuator 28 in a ratchet system 27, an electrical stimulator in the form of implantable electrical neural stimulator (INS) 29, and lead 30. An introducer 31 may be used to introduce IMD 24 into the body of a patient. IMD 24 may be used by a surgeon to locate a nerve in pelvis 10 for the purpose of implanting lead 30 that stimulates the nerve with INS 29. Lead 30 covered by introducer 31 (e.g., a sheath) in the example of FIG. 1, is inserted through sacral foramen 20 to access sacral nerves of a patient. In this manner, lead 30 supports access to the sacral nerves. Pelvic nerves may include sacral nerves, pudendal nerves, or branches of pudendal nerves, and other pelvic nerves. Upon placing lead 30 adjacent a suitable nerve site, IMD 24 may be implanted chronically (e.g., for weeks, months, or years) or temporarily (e.g., for hours, days, or weeks) within the patient to deliver long term or short-term electrical stimulation therapy. Short-term therapy may include trial therapy to evaluate prognostic efficacy of the electrical stimulation therapy or therapy of a prescribed short-term duration. IMD 24 may be explanted from the patient, or left implanted, upon completion of the short-term therapy.

IMD 24 may be used to reach a wide variety of nerves which can be accessed by the surgical procedure described herein. Pelvic floor stimulation will be described for purposes of example, but without limitation as to the use of IMD 24 in other stimulation applications, such as for spinal cord stimulation (SCS), peripheral nerve stimulation (PNS), peripheral nerve field stimulation (PNFS), deep brain stimulation (DBS), cortical stimulation (CS), gastric stimulation, and the like.

For pelvic floor stimulation, example nerve targets include the sacral nerve, the pudendal nerve, various branches of the pudendal nerve, the nerve of the clitoris, as well as other pelvic nerves. IMD 24 may be implanted within a patient with lead 30 positioned proximate a target nerve or nerves within pelvis 10. In some cases, the shape of IMD 24 may be modified to facilitate lead placement proximate a target nerve or nerves. For example, a tip of lead 30 may be deflected with deflection actuator 28 and ratchet system 27 to facilitate lead placement proximate a target sacral nerve or other nerve located within the pelvis. In this example, the deflection of lead 30 may cause the distal tip of lead 30, and introducer 31, to change from a first shape to a second shape. Upon location of a distal end of lead 30 proximate to the target nerve or nerves, introducer 31 may be removed from lead 30 and IMD 24 may be implanted in the patient. Introducer 31, or any other introducer described herein, may be any object that is introduced into or otherwise penetrates tissue of the patient and provides an insertion channel for lead 30 and/or housing 26 to travel into the patient.

In the example of pelvic floor implantation, the sacral nerves are found within sacrum 14 and exit the sacrum anterior through a foramen (hole). The sacral nerves exit laterally and caudally from the sacral foramen. Minimally invasive methods for implanting an electrical lead adjacent the sacral nerve are preferred, but may be difficult to perform. In addition, the use of imaging equipment to implant the electrical lead may be cumbersome or impractical in some cases. Advantageously, unlike a straight needle, using the method and device described in this disclosure, a physician may be able to deflect the tip of lead 30 with deflection actuator 28 to accurately locate the tip of lead 30 adjacent to the sacral nerve. In this manner, IMD 24 allows the physician to successfully locate the sacral nerve, effectively positioning the lead 30 adjacent the sacral nerve, remove introducer 31 from lead 30, and implant IMD 24.

A procedure using IMD 24 is preferably performed on a patient having normal anatomical soft tissue covering pelvis 10 such as muscle, blood vessels, organs, and skin. FIG. 1 is for illustrative purposes and shows pelvis 10 without soft tissue surrounding pelvis 10. Local or general anesthetics may be administered to minimize pain perceived by the patient.

Introducer 31 of lead 30 may pierce skin in the lower back of the patient. Once underneath the skin, the physician may advance lead 30 of IMD 24 in the direction of the arrow through sacral foramen 20 to the approximate location of the sacral nerve. In some examples, the physician may deflect the tip of lead 30 with deflection actuator 28 and ratchet system 27 to better locate lead 30 adjacent to the target nerve site. In the case of different nerves, i.e., other than the sacral nerve associated with sacral foramen 20, a different deflection of a portion of lead 30 near a distal tip of lead 30, relative to a major longitudinal axis of the lead, may aid in directing lead 30 to the appropriate nerve site. Hence, where lead 30 may have a major longitudinal axis, deflection may refer to at least some deviation from the major longitudinal axis. If the longitudinal axis of lead 30 is assumed to be at a reference angle of 0 degrees, the deflection may result in deviation of a distal portion of the lead 30 by an angle of in a range of approximately 10 degrees to 60 degrees, and in another example, 35 degrees to 55 degrees, relative to the reference angle of the major longitudinal axis. In some examples, deflection may result in one or more electrodes being displaced from the major longitudinal axis by a distance in the range of 0.1 mm to 20 mm, and in another example, 0.5 mm to 1.5 mm.

For example, in the case of deflecting the distal portion of lead 30 to be adjacent to a sacral nerve, the sacral nerve may divert from the foramen axis by approximately 45 degrees. Thus, if lead 30 is placed such that its major longitudinal axis is substantially aligned with an axis passing through the foramen at an angle substantially perpendicular to the major plane of the foramen opening, the distal portion of the lead 30 may be deflected by an angle of approximately 45 degrees in order to position the distal portion adjacent to the sacral nerve. If lead 30 is positioned such that the major longitudinal axis is not substantially aligned with the foramen axis, the distal portion of lead 30 may need to be deflected substantially more or less than 45 degrees relative to the foramen axis in order to position the distal portion of lead 30 adjacent to the sacral nerve.

Housing 26 is shaped to allow a physician to hold it with at least one hand. Ratchet system 27 and deflection actuator 28 are also provided to support the deflection of the distal end of lead 30. Ratchet system 27 may be configured to allow a physician to deflect the tip of lead 30 with one hand and retain the deflection curve of lead 30 until the physician intentionally adjusts deflection actuator 28. In other words, ratchet system 27 prevents or minimizes unintentional changes to the deflected tip of lead 30. This may be particularly important after implantation to prevent unwanted changes in the deflection of the tip of lead 30. In some examples, ratchet system 27 may comprise a ratchet system or any other mechanical device that allows motion, e.g., linear or rotational, in one direction while preventing motion in the opposite direction. For example, ratchet system 27 may allow deflection actuator 28 to move in one direction while preventing deflection actuator 28 from moving in the opposite direction until a physician disengages or unlocks ratchet system 27. In some examples, a mechanism other than ratchet system 27 may lock deflection actuator 28. In general, actuator 28 may travel between a first position at which the lead tip is not deflected and a second position at which the lead tip is fully deflected. In some examples, actuator 28 may be configured to travel entirely from the first position to the second position, and vice versa, or stop at intermediate positions, corresponding to different degrees of deflection, during travel between the first and second positions.

Deflection actuator 28 may be integrated with housing 26 in IMD 24 and may remain within IMD 24 within the patient following implantation. Deflection actuator 28 may be constructed of a soft rubber or plastic so that the physician's thumb does not slip during the procedure. Other ergonomic features of housing 26 may be provided as well. For example, the sides of housing 26 may follow the contours of a hand or fingers. In addition, soft or rubber pads may be placed where housing 26 contacts with the hand to provide a secure gripping surface. In some examples, deflection actuator 28 may actuate a pull-wire that is ratcheted by ratchet system 27. For example, when deflection actuator 28 is moved from a first position to a ratcheted position of ratchet system 27, deflection actuator 28 may pull (e.g., increase tension) on the pull-wire. As described in further detail below, the pull-wire may be connected to the distal tip of lead 30 and, when pulled, may cause the tip of the lead to deflect. In this way, deflection actuator 28 may actuate the pull-wire to deflect the tip of the electrical lead 30. Likewise, deflection actuator 28 may be pushed to thereby push the pull-wire and move the tip toward a non-deflected position, such as a straightened position relative to a major longitudinal axis of the lead. Alternatively, deflection actuator 28 and ratchet system 27 may be arranged in an opposite manner to that described above, such that pushing of the deflection actuator 28 causes deflection of the distal tip of the lead 30 and pulling of the deflection actuator 28 causes the distal tip of the lead 30 to move toward a non-deflected, e.g., straightened, position. In either case, increasing pulling tension or pushing pressure on the pullwire increases deflection of the tip of lead 30. Releasing tension on the pullwire may decrease deflection of the the tip of the lead 30. Deflection actuator 28 may be provided as an integral component within housing 26 that may be implanted along with housing 26 in IMD 24.

In some examples, ratchet system 27 may allow for movement of the actuator 28 in one direction while preventing movement in the opposite direction. For example, ratchet system 27 may allow for incremental translation of actuator 28 in a proximal or distal direction while preventing reversal of the movement, thus allowing deflection of lead 30 without allowing reversal of the deflection. Ratcheting system 27 may include a linear rack of teeth and a spring-loaded pawl, coupled to or a part of actuator 28, that engages with the teeth. The teeth of the track may be asymmetrical to allow for the pawl to advance over the teeth in one direction but not the other and thus allow movement of actuator 28 in one direction and not the other.

In certain examples, actuator 28 may be released from the ratcheting system to allow, for example, straightening of the lead 30. This may be desirable in cases where a physician, for example, has determined that it has displaced the lead 30 too far. Ratchet system 27 may include a trigger system that may engage with the pawl to release the pawl from engagement with the teeth of the track such that actuator 28 may move in either a proximal or distal direction. In some examples, the trigger system may engage with the track to displace the track from engagement with the pawl to allow for movement of actuator 28 in either a proximal or distal direction.

In some examples, ratchet system 27 may lock actuator 28 in place, and therefore lock in place the deflection of the tip of lead 30 unless a sufficient amount of force is applied to actuator 28 to enable actuator 28 to be moved to a next position corresponding to a next position of deflection for the tip of lead 30. For example, actuator 28 may be coupled to or comprise the pawl and the pawl may engage with the teeth of the track of ratchet system 27 at a plurality of positions along a thumb (or finger) slide. Each position between a pair of teeth may receive the pawl of actuator 28 to engage the actuator 28 at a corresponding position along the slide.

Additionally, a locking mechanism may include one or more springs for maintaining the pawl in a particular position, and thus locking the pawl, the actuator, and the distal portion of lead 30 in place, and/or for allowing the pawl to advance to different positions and thus unlocking the pawl, actuator, and the distal portion.

The teeth may be configured to provide resistance to movement along the slide. For example, the teeth may be of a shape and/or material to provide resistance of movement past each tooth of the track. For example, when the pawl of actuator 28 are engaged with a particular position between a pair of teeth, sufficient force may need to be applied to actuator 28 to release the pawl of the actuator 28 from the position and past the next tooth to advance the actuator 28. Each position between a pair of teeth on the track may correspond to a different deflection angle of the tip of lead 30. Thus, a physician may need to apply a sufficient amount of force to overcome the next tooth in the current position and advance the actuator 28, and therefore the tip of lead 30, to the next position. The amount of force required to advance the actuator 28 from one position to the next may be an amount that may easily be applied by the physician but not likely to be applied accidentally by the physician or by collision of the actuator 28 with tissue of the patient.

Each time that the actuator 28 is advanced and locked into a position, the advancement and locking mechanism of ratchet system 27 may provide tactile feedback to the physician to help the physician recognize advancement of the actuator 28 and corresponding deflection of the tip of lead 30 to assist with efficient implantation. For example, acceleration out of each position and deceleration into the next while a physician's hand is in contact with the actuator 28 may provide tactile feedback to the physician. Alternatively or in addition, the physician may receive auditory feedback in the form of a "click" or other noise indicating advancement to a new position. Housing 26 may also include markers along side ratchet system 27 such that advancement of actuator 28 to a new position results in placement of actuator 28 next to a corresponding marker, providing visual feedback to the physician. Thus, ratchet system 27 may provide tactile, auditory, and/or visual feedback to the physician to indicate each of the plurality of ratchet positions. In these examples, the tactile feedback, auditory feedback, and/or visual feedback from ratchet system 27 to the physician may also be an indication of the amount of deflection of the distal end of electrical lead 30.

Lead 30 of IMD 24 may be covered by introducer 31 (e.g., a sheath) when inserted into pelvis 10. Introducer 31 may be constructed of an injection moldable plastic such as polystyrene, polypropylene, polycarbonate, or any other polymer. In some examples, lead 30 may be covered at least in part by introducer 31. Additionally or alternatively, in some examples, introducer 31 may be removable. For example, introducer 31 may be split apart, i.e., slit, after location of the distal tip of lead 30 near the sacral nerve. Slitting may permit the introducer 31 to be withdrawn over the INS housing 26, which may have a significantly larger size than the lead 30. In this manner, once lead 30 is appropriately positioned near the sacral nerve, introducer 31 is removed from lead 30 so that lead 30 remains positioned adjacent to the sacral nerve. Additional information regarding, for example, an introducer or a removable introducer may be found in U.S. Patent Application Publication No. US20130110201 A1, to Bonde et al., filed May 2, 2013, entitled "Medical Devices for Trial Stimulation," the entire contents of which being incorporated herein by reference.

In some examples, prior to removing introducer 31 from around lead 30, a physician may use INS 29 connected to the one or more electrode of lead 30 to perform test stimulation to confirm the capture of the target nerve by electrical stimulation pulses. For example, introducer 31 may have window-like apertures that allow the one or more electrodes at the distal end of lead 30 to protrude through the introducer to engage patient tissue and thereby deliver stimulation energy to perform the test stimulation. Additionally or alternatively, in some examples, introducer 31 may be comprised of an electrically conducting material that allows some or all of the one or more electrodes at the distal end of lead 30 to deliver stimulation energy to perform test stimulation. In some examples, introducer 31 may include a sleeve with one or more electrically insulating portions that may be rotated into occlude one or more electrodes at the distal end of lead 30, the apertures of introducer 31, and/or the electrically conducting material of introducer 31 after test stimulation is complete.

After confirming lead 30 has been placed near the sacral nerve, e.g., by monitoring sensed signals or observing outward symptoms resulting from effective placement of the lead for stimulation, the physician may remove introducer 31. In some examples, removal of introducer 31 may allow lead 30 to be secured in place, e.g., with tines or other anchoring structures that may expand outward from the lead upon withdrawal of the introducer 31 and be embedded within tissue of the patient. For example, tines may be disposed within a muscle covering sacral foramen 20. Tines on the lead 30 may also be attached to other surrounding tissue.

In some examples, during evaluation of stimulation therapy, housing 26 of IMD 24 may be external to the patient, and at least a portion of the lead 30 may exit the patient's skin when attached to housing 26 of IMD 24. In these examples, the physician may evaluate stimulation therapy with IMD 24 prior to implantation. In some examples, the lead 30 may be pre-connected to INS 29, such that a physician is not required to connect the lead 30 to INS 29. In some examples, lead 30 may be packaged with introducer 31 covering lead 30. In other examples, a physician may cover the lead 30 with introducer 31.

In this manner, in some examples, after a successful evaluation of the stimulation therapy, the physician may implant IMD 24 including INS housing 26 within the patient. In other examples, after an unsuccessful evaluation of the stimulation therapy, the physician may reposition IMD 24 by repositioning housing 26 and/or changing the deflection of lead 30 using the technique described herein iteratively until a successful evaluation is achieved and may then implant IMD 24, including INS housing 26, within patient. In other examples, IMD 24, including lead 30, may be removed from the patient and a new device may be positioned and implanted according to particular needs.

The location of the implanted IMD 24 may vary according to the health, condition, and/or anatomy of the patient. Examples of possible locations for a chronic stimulator may include the lower back, buttocks, abdomen, or thigh. In each case, electrical stimulation is delivered through the one or more electrodes on lead 30 implanted adjacent to the sacral nerve via the technique described in this disclosure. INS 29 may be programmed to deliver electrical stimulation therapy appropriate for treatment of urinary incontinence, sexual dysfunction, pelvic pain, or other disorders. In addition, IMD 24 may be implanted in any suitable location in the body according to particular needs and INS 29 may be programmed deliver electrical stimulation therapy appropriate for any suitable type of treatment according to particular needs.

In some examples, one or more components of IMD 24 may be reusable to reduce equipment costs. For example, IMD 24 may be reusable as it may be removed after an initial implantation and re-implanted. In some examples, even though lead 30 may be pre-connected to housing 26, lead 30 may be detachable. In some cases, lead 30 may be disposable. Alternatively, lead 30 may be autoclaved or radiologically or chemically sterilized for use in implanting lead 30 into a different patient. A new or sterilized lead 30 may be attached to housing 26 to form the integrated IMD 24 comprising the lead 30, INS 29, and actuator 28 for implantation within a patient.

Figure 2:
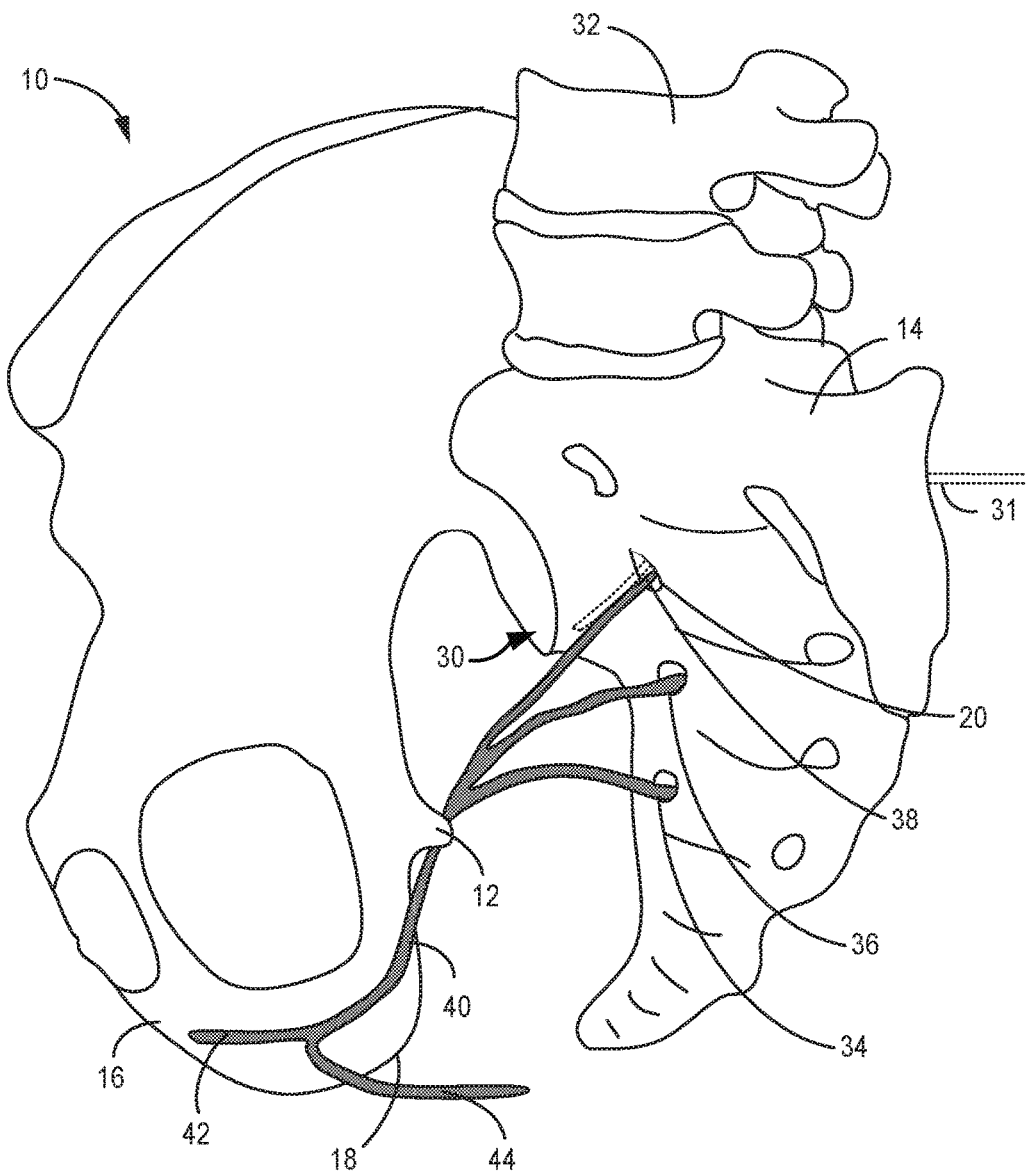
FIG. 2 is a schematic diagram illustrating the exemplary deflecting tip of the lead of FIG. 1 upon insertion through the sacral foramen to reach a sacral nerve.

FIG. 2 is a schematic diagram illustrating the exemplary deflecting tip of lead 30 of FIG. 1 upon insertion through sacral foramen 20 to reach sacral nerve 38. In the example of FIG. 2, pelvis 10 includes sacrum 14, inferior pubic ramus 16, ischial tuberosity 18, sacral foramen 20, and ischial spine 12. FIG. 2 shows an interior view of pelvis 10. Vertebrae 32 are attached to sacrum 14 and protect the spinal cord (not shown) as it travels from the brain to pelvis 10. Sacral S2 nerve 34, sacral S3 nerve 36, and sacral S3 nerve 38 emanate from the spinal cord out from sacrum 14. Sacral nerves 34, 36, and 38 combine posterior of ischial spine 12 to form pudendal nerve 40. Pudendal nerve 40 branches into perineal branch 42 and anal branch 44. Lead 30 is shown, covered by introducer 31, tunneled through sacral foramen 20 into the interior of pelvis 10 and adjacent to sacral S3 nerve 38.

Sacral S3 nerve 38 (also described as "sacral nerve 38") may be difficult to access using surgical techniques as it is located on the anterior side of sacrum 14. Sacral nerve 38 is surrounded by other nerves and important tissues, so accurate guidance of lead 30 may be difficult without internal guides when inserting lead 30. Additionally, sacral foramen 20 is smaller in diameter than the obturator foramen and may be more difficult to navigate. To aid in insertion, the physician may palpate structures of pelvis 10, use tactile feedback, or other landmarks of pelvis 10 to locate sacrum foramen 20 or any other sacrum foramen. In some examples, a physician may use fluoroscopy and/or ultrasound to locate sacrum foramen 20.

Inserting lead 30 into pelvis 10 with a procedure as described herein may be beneficial over other methods to reach sacral nerve 38. Because there are no nerves passing over sacral foramen 20, it is unlikely that lead 30 would disturb another nerve near sacral nerve 38. In addition, the physician needs only a simple hand motion to insert lead 30 adjacent to sacral nerve 38. Anatomical structures may also aid in guiding lead 30 to the correct location.

While the shape of lead 30 simplifies sacral nerve isolation, other techniques may be useful in fine adjustment of the position of lead 30. Instead of using strictly anatomical landmarks to position lead 30 adjacent to sacral nerve 38, imaging techniques such as fluoroscopy may be used in some examples. The physician also may rely on tactile feedback to guide placement, e.g., from lead 30 contacting ligaments, muscle bones or other structure. Alternatively, or additionally, IMD 24 may use INS 29 as a test stimulator (not shown in FIG. 2) that produces electrical stimulation to verify accurate lead placement relative to the sacral nerve. For example, as will be described in greater detail, IMD 24 may include an electrical stimulation pulse generator in INS 29 electrically coupled to electrodes carried by lead 30 via electrical conductors.

Lead 30 may have one or more electrodes near the distal tip of lead 30 to deliver electrical pulses to sacral nerve 38. Lead 30 may include conductors coupling the one or more electrodes and to contacts at or near a proximal end of lead 30. The contacts may be coupled to electrical circuitry of INS 29 to allow INS 29 to provide stimulation energy to the electrodes of lead 30 for stimulation of tissue proximate to lead 30.

Lead 30 may include one or more electrodes arranged for unipolar, bipolar, and/or multipolar stimulation. For example, lead 30 may include one or more electrodes at or proximal to its tip and housing 26 may house at least one electrode used for unipolar stimulation with the at least one or more electrodes of lead 30. As another example, lead 30 may include a plurality of electrodes used for bipolar and/or multipolar stimulation. As another example, lead 30 may include a plurality of electrodes used selectively for unipolar stimulation, with one or more electrodes within housing 26, or for bipolar or multipolar stimulation. Any suitable combination of electrodes on lead 30 or in housing 26 may be used for unipolar, bipolar, and/or multipolar stimulation according to particular needs.

Preferably, the majority of lead 30 may be electrically insulated so that stimulation energy can be generally confined to the tip of lead 30. Hence, the one or more electrodes may be provided by an electrically conductive lead 30 as described in FIG. 3 below. In certain examples, as described below with reference to FIGS. 4A-4C, one or more dedicated testing electrodes may be formed at or near a distal tip of introducer 31, e.g., by deposition, crimping, welding, or other fabrication techniques, for use in testing placement of lead 30 before removal of introducer 31. Introducer 31 may have window-like apertures that allow the one or more electrodes at the distal end of lead 30 to protrude through the introducer to engage patient tissue and thereby deliver stimulation energy to perform the test stimulation. Additionally or alternatively, in some examples, introducer 31 may be comprised of an electrically conductive material that allows some or all of the one or more electrodes at the distal end of lead 30 to deliver stimulation energy to perform test stimulation. Thus, the physician may be able to deliver stimulation energy to test the placement of lead 30 while introducer 31 is still at least partially surrounding lead 30.

Upon delivery of test stimulation energy to the one or more electrodes of introducer 31 or lead 30, the physician may identify muscle movement associated with appropriate sacral nerve stimulation to correctly place lead 30. Alternatively, electromyography may be performed with INS 29 operating as the test stimulator to observe a compound muscle action potential (CMAP) which aids in correct placement of lead 30. In either case, INS 29 operating as the test stimulator aids the physician in positioning lead 30 relative to sacral nerve 38.

Introducer 31 may be located around lead 30, and utilized when implanting lead 30. Lead 30 may reside within an inner lumen defined by the introducer 31. The distal tip of lead 30 may be recessed from a distal end of introducer 31. The distal tip of introducer 31 may provide a sharp point for penetration of tissue during the approach to the sacral nerve 38. In other examples, introducer 31 covering lead 30 may comprise a dull or blunt point to limit tissue damage from contact with a sharp point. Once lead 30 is positioned correctly, introducer 31 may be removed from lead 30 such that lead 30 remains in place and the distal end of the lead 30 remains adjacent to sacral nerve 38. Lead 30 may also be moved slightly after removal of introducer 31 for fine adjustment of the placement location. In some cases, the physician may deflect the distal tip lead 30 to customize the shape of lead 30 to target a desired nerve site. In some examples, as an alternative or in addition to an introducer, lead 30 may include an internal stylet for facilitating placement of lead 30 within the tissue and an introducer 31.

In other examples, IMD 24 may be used to access other nerves in pelvis 10. For example, lead 30 of IMD 24 may be inserted though sacral foramen 20 to reach the nerve of the clitoris located near inferior pubic ramus 16. IMD 24 may also be used to implant lead 30 near perineal branch 42 or anal branch 44 of pudendal nerve 40. Lead 30 may be shaped slightly differently (e.g., with different deflection curves) to access nerves other than sacral nerve 38. In other examples, IMD 24 may be used to access nerves or other stimulation targets in other areas of the body.

Figure 3:
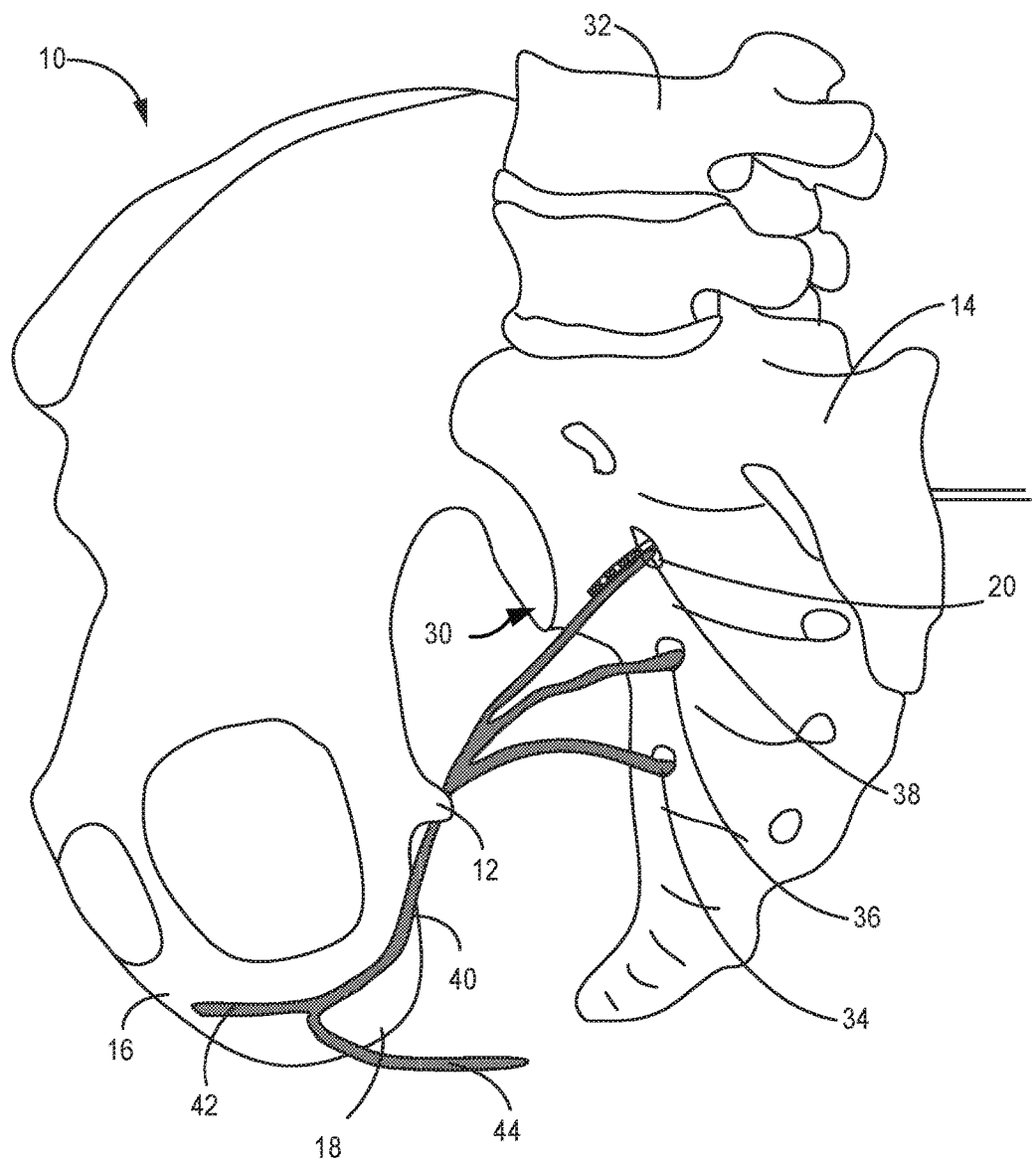
FIG. 3 is a schematic diagram illustrating an exemplary electrical lead of the IMD of FIG. 1 inserted through the sacral foramen and disposed adjacent to a sacral nerve after removal of an introducer.

FIG. 3 is a schematic diagram illustrating an exemplary lead 30 of IMD 24 of FIG. 1 implanted through sacral foramen 20 and disposed adjacent to sacral nerve 38 after removal of introducer 31. In some examples, electrical lead 30 of IMD 24 may correspond to lead 30 of IMD 24 as described in FIGS. 1 and 2.

As shown in FIG. 3, lead 30 is implanted adjacent to sacral nerve 38 in pelvis 10. As described in FIGS. 1 and 2, introducer 31 may be used to guide lead 30 adjacent to sacral nerve 38, e.g., for delivery of stimulation energy to alleviate urinary incontinence, fecal incontinence, or sexual dysfunction. In some examples, after removal of introducer 31, test stimulation may be delivered from INS 29 of IMD 24, to ensure the one or more electrodes at the distal end of lead 30 are located in a correct position relative to sacral nerve 38. If the location of lead 30 is incorrect, lead 30 may be adjusted, either longitudinally or rotationally, with the housing 26 of IMD 24, to provide better electrical contact between the one or more electrodes carried by lead 30 and sacral nerve 38.

In the example of FIG. 3, introducer 31 has been removed, leaving lead 30 disposed within a tunnel previously created by introducer 31. Lead 30 may include tines or other structure to anchor lead 30 within tissue of pelvis 10. The procedure for lead implantation provides secure anchoring tissue for the tines of lead 30. For example, tines may be secured within the muscle covering sacral foramen 20. Anchoring lead 30 within the muscle covering sacral foramen 20 may limit the amount of movement of lead 30 away from sacral nerve 38. In some examples, other anchor mechanisms may be needed to secure lead 30 within the patient. Some example anchor mechanisms may include screws, porous structures that allow tissue in-growth, or sutures.

In some examples, lead 30 may be pre-connected to INS 29, which may operate as a trial and/or chronic electrical stimulator. In some examples, lead 30 may be coupled to INS 29 external to the patient. When INS 29 is external to the patient, INS 29 may be used as a trial stimulator and permit the physician and the patient to evaluate stimulation efficacy before finalizing the implantation of IMD 24. In some examples, if stimulation therapy is unsuccessful, the physician may further adjust lead 30 of IMD 24. In other examples, if stimulation therapy is unsuccessful, the physician may remove lead 30 from the patient. In these examples, the physician may repeat the implantation technique as described herein until the stimulation therapy is successful.

In some examples, if stimulation therapy is tested and confirmed to be successful or if testing is not required, IMD 24 may be implanted beneath the skin of the patient. When INS 29 is internal to the patient, INS 29 may operate as a chronic stimulator, which may provide, for example, months or years of stimulation therapy with the use of lead 30. Lead 30 may be used by INS 29 when operating as a trial stimulator or a chronic stimulator.

INS 29 within housing 26 of IMD 24 may be located at a variety of locations within the patient. Preferably, housing 26 may be located near lead 30 and in a location that does not interfere with patient activity. For example, housing 26 may be located in the abdomen, buttocks, lower back, or thigh. In any location, lead 30 may be of sufficient length to reach sacral nerve 38 while coupled to INS 29.

In other examples, the distal end of lead 30 may be positioned adjacent other sacral nerves. For example, lead 30 may be inserted with a distal end positioned adjacent the nerve of the clitoris, e.g., for delivery of electrical neurostimulation to alleviate symptoms of sexual dysfunction or incontinence. In any nerve location, lead 30 may be implanted through sacral foramen 20. In some examples, however, lead 30 may not be tunneled through sacral foramen 20.

In cases using IMD 24 for stimulation in other areas of the body, IMD 24 may be implanted in areas that preferably do not interfere with patent activity and allow for lead 30, being of any suitable length, to reach the targeted stimulation area.

Figure 4A:
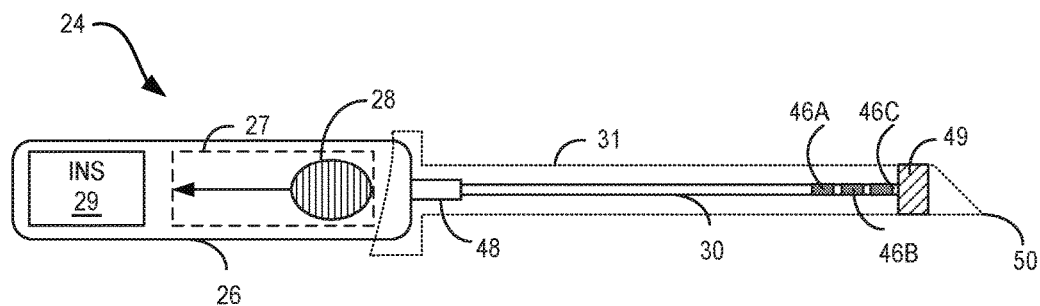
FIGS. 4A and 4B are views of an exemplary IMD with a lead having a deflecting tip and a sliding actuator configured to cause the tip of the lead to deflect to implant the lead adjacent to a nerve.
Figure 4B:
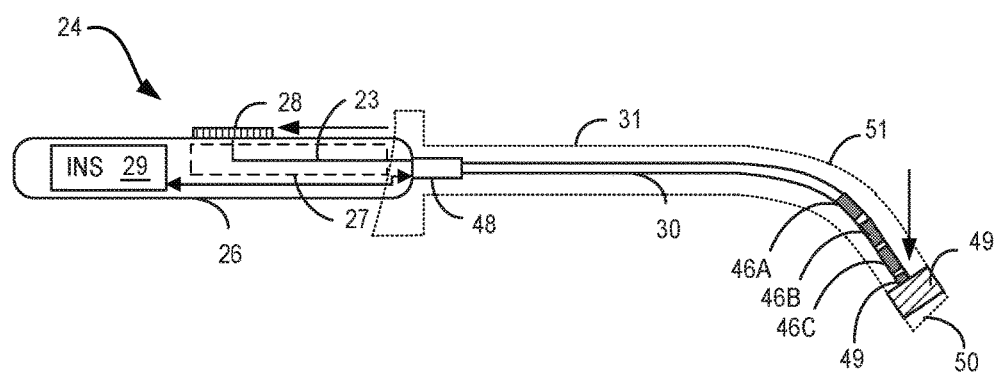

FIGS. 4A and 4B are views of an exemplary IMD 24 with lead 30 having a deflecting tip and a sliding actuator 28 configured to cause the tip of lead 30 to deflect to implant the lead 30 adjacent to a nerve. As shown in the top view of FIG. 4A, IMD 24 includes housing 26, ratchet system 27, deflection actuator 28, INS 29, lead 30, and neck 48. Additionally, introducer 31 may surround at least a portion of lead 30 and may include section 49 and introducer tip 50. In some examples, IMD 24, including housing 26, ratchet system 27, deflection actuator 28, INS 29, and lead 30, and introducer 31 surrounding lead 30 may correspond to IMD 24, including housing 26, ratchet system 27, deflection actuator 28, INS 29, and lead 30, and introducer 31 surrounding lead 30 as described in FIG. 1.

In the example of FIGS. 4A and 4B, housing 26 is generally rectangular in shape and has curved edges. Neck 48 securely attaches electrical lead 30 to housing 26. Neck 48 may provide an attachment mechanism to enable electrical lead 30 to be removed from neck 48. For example, neck 48 may include spring-loaded terminals, set screws, or any other suitable mechanism for allowing removal of lead 30 from neck. Additionally, neck 48 may reduce strain on lead 30. Detachment of lead 30 may be necessary if lead 30 is to be disposable or sterilizable separate from housing 26. Alternatively, neck 48 may be permanently attached to electrical lead 30 and neck 48 is removable from housing 26 by, for example, spring-loaded terminals, set screws, or any other suitable mechanism for removable attachment. In some examples, electrical lead 30 may be pre-connected and/or permanently affixed to INS 29 of IMD 24. In some examples, neck 48 may be pre-connected and/or permanently affixed to housing 26 of IMD 24. In other words, electrical lead 30 and neck 48 may be connected and secured to housing 26 of IMD 24 during manufacturing, such that the physician is not required to make any physical or electrical connection between electrical lead 30, INS 29, and housing 26 of IMD 24.

Lead 30 may include one or more electrodes 46A-C. The one or more electrodes 46A-C may be unipolar, bipolar, or multipolar and may be ring electrodes, pad electrodes or segmented electrodes or any suitable combination of different types of electrodes. Lead 30 may include conductors for coupling the one or more electrodes 46A-C to terminals at or proximal to the distal end of lead 30 coupled to INS 29.

Introducer 31 of lead 30 may facilitate entry through the tissue of the patient and enables access to sacral nerve 38. In some examples, introducer tip 50 may be used to pierce tissue and create a tunnel through pelvis 10. Introducer tip 50 may be shaped similar to a wedge, cone, pyramid, or any other shape that includes decreased surface area at the distal end of introducer 31 to define a sharp point.

Section 49 of introducer 31 may be located near or on tip 50 for test stimulation during placement of lead 30. In some examples, section 49 may include one or more distal electrodes formed on introducer 31 and connected to INS 29 to perform test stimulation. In other examples, section 49 of introducer 31 may be a window-like aperture that exposes a selected portion of lead 30 and defines one or more electrode regions either at distal tip 50 or displaced some distance from distal tip 50 that allow one or more electrode of electrodes 46A-C of lead 30 to protrude to stimulate tissue outside of introducer 31. In yet other examples, section 49 may be an electrically conductive material that allows some or all of the one or more electrodes 46A-C on lead 30 to perform test stimulation while introducer 31 is still at least partially surrounding lead 30. Section 49 may be cylindrical, circular, or rectangular in shape. Alternatively, in some examples, introducer 31 may have more than one section 49. In these examples, the majority of introducer 31 may be an electrically insulative sheath or sleeve. In some examples, section 49 may be located at a distal end of introducer 31 and coupled to an electrical conductor within electrical lead 30. In some examples, section 49 may be one of a plurality of sections of introducer 31 including one or more test electrodes on introducer 31 or allowing for exposure of the one or more electrodes 46A-C on lead 30 to tissue.

In some examples, introducer 31 may be hollow and open at tip 50. In these examples, a hollow introducer 31 may permit the flow of a fluid to the tissue to lubricate or anesthetize the surrounding tissue or reduce tissue damage as introducer 31 is inserted into the patient.

Lead 30 may vary in length. Different sized patients may require different sizes of lead 30. In general, the length of lead 30 may be in a range of approximately 1 cm to 50 cm. More specifically, the length of lead 30 may be in a range of approximately 10 cm to 20 cm. In some cases, the length of lead 30 may be approximated by the height of the patient. In other cases, one length of lead 30 may be appropriate for any sized patient. Generally, the diameter of lead 30 may be in a range of approximately 0.5 mm to 3.0 mm.

In some examples, housing 26 may be formed in a cylindrical, spherical, or other ergonomic shape designed to be held by one hand. A generally cylindrical housing 26 shape may provide the most flexibility to a physician using IMD 24. In other words, the physician may hold housing 26 at any circumference to direct lead 30 to any location. A cylindrical housing shape may also allow the physician to easily manipulate IMD 24 when attempting to position and deflect lead 30 near sacral S3 nerve 38. For example, the physician may readily move housing 26 longitudinally and rotationally, as needed, during the process.

Housing 26 may generally be in a range of approximately 10 mm to 30 mm in length, 0.5 mm to 10 mm in width, and 0.5 mm to 5 mm in thickness. Preferably, housing 26 may be in a range of approximately 10 mm to 15 mm in length, 2 mm to 4 mm in width, and 1 mm to 3 mm in thickness. Housing 26 may be provided in different sizes to accommodate INS 29 and different sized hands of varying physicians. In addition, housing 26 may be made to accommodate use in a right or left hand, either as ambidextrous or separate models.

Housing 26 may be constructed of an injection moldable plastic such as polystyrene, polypropylene, polycarbonate, or any other polymer. In some examples, housing 26 may be constructed of a metal alloy including stainless steel, titanium, aluminum, or a composite material. The material used to construct housing 26 may be dependent on the intended life of IMD 24.

In some examples, introducer 31 may be constructed of a plastic material. In these examples, an electrical conductor may be provided within introducer 31 for conduction of stimulation energy to one or more electrodes (e.g., section 49) formed at or adjacent to distal tip 50 of introducer 31. For some examples, one or more electrodes 46A-C on electrical lead 30 may act as an electrical conductor within introducer 31 for conduction of stimulation energy to the one or more electrodes of introducer 31. Electrodes formed at or adjacent to distal tip 50 of introducer may be unipolar, bipolar, or multipolar.

In some examples, the outer layer of lead 30 may be constructed of a polymeric material such as polyurethane or poly(dimethyl siloxane), a fluoropolymer, and/or co-polymers including any combination of these materials. In these examples, one or more electrical conductors may be provided within lead 30 for conduction of stimulation energy from INS 29 to one or more electrodes 46A-C formed at or adjacent to distal tip 50 of introducer 31. As illustrated in FIG. 4A, deflection actuator 28 may be in a first position when the distal end of electrical lead 30 is not deflected. However, in some examples, the distal end of electrical lead 30 may be deflected by a physician with deflection actuator 28.

In operation, in some examples, a physician may penetrate a sacral foramen with distal tip 50 of introducer 31 and translate deflection actuator 28 on housing 26 to deflect electrical lead 30 within introducer 31. In these examples, the physician may move lead 30 into the interior of the pelvis such that distal tip 50 of introducer 31 is placed adjacent to a desired nerve site (e.g., the sacral nerve). In some examples, deflection actuator 28 may also have a locking mechanism, in addition to ratchet system 27, discussed above with reference to FIG. 1, which can lock the deflection caused by deflection actuator 28. For example, deflection actuator 28 may be translated to deflect the distal end of lead 30 and rotated to lock in place the deflection caused by the translation of deflection actuator 28. For example, actuator 28 may be rotated so that actuator 28 no longer engages with the thumb (or finger) slide described, above with reference to FIG. 1, but instead engages with a stop that prevents translation of actuator 28 with respect to housing 26.

In some examples, after locking deflection actuator 28, the physician may remove introducer 31 from the patient and implant IMD 24 into the patient. Additionally, in some examples, after implantation of IMD 24, the physician may later remove the implanted IMD 24 from the patient and unlock deflection actuator 28 in order to change the deflection of the distal end of electrical lead 30. In these examples, the change in the deflection of the distal end of electrical lead 30 may lead to a better placement of electrical lead 30 near the sacral nerve.

For example, as illustrated in FIG. 4B, deflection actuator 28 may be actuated (e.g., translated) to a position other than the first position to deflect the distal end of electrical lead 30. In some examples, deflection actuator 28 may be connected to a pull-wire within ratchet system 27. Ratchet system 27 may allow deflection actuator 28 to ratchet the pull-wire at a plurality of ratchet positions, thereby deflecting the distal end of lead 30 according to the plurality of ratchet positions. Advancing the actuator 28 to each position within ratcheting system 27 may result in tactile feedback, in the form of acceleration out of each position and deceleration into the next while a physician's hand may be in contact with the actuator, and/or auditory feedback, in the form of a "click" or other noise indicating advancement to a new position. Housing 26 may also include markers along side ratchet system 27 such that advancement of actuator 28 to a new position results in placement of actuator 28 next to a corresponding marker, providing visual feedback to the physician. Thus, ratchet system 27 may provide tactile, auditory, and/or visual feedback to the physician to indicate each of the plurality of ratchet positions. In these examples, the tactile feedback, auditory feedback, and/or visual feedback from ratchet system 27 to the physician may also be an indication of the amount of deflection of the distal end of electrical lead 30.

Deflection actuator 28 may be constructed of a soft rubber or other elastomeric material to provide comfort and friction between the thumb of a physician and deflection actuator 28. As shown between FIGS. 4A and 4B, movement of actuator 28 to the position shown in FIG. 4B may cause lead 30 to be deflected to form bend 51. In some examples, electrical lead 30 may have magnetic resonance imaging (MM) shielding (e.g., an Mill braid) that may increase the stiffness of electrical lead 30 up to bend 51 so actuation of deflection actuator 28 may cause the distal end of electrical lead 30 to deflect and form bend 51. In some examples, deflection actuator 28 may also indicate the deflection orientation of the distal end of electrical lead 30. In some examples, lead 30 may have a radius of curvature about bend 51 in a range of approximately 1 mm to 40 mm, and more preferably approximately 1.5 mm to 25 mm, to permit ease of insertion to the desired nerve site. In some examples, bend 51 may be located closer or further from electrodes 46A-46C. In some examples, bend 51 may be proximate to electrodes 46A-46C, and the radius of curvature may be in the range of approximately 5 mm to 15 mm. In some examples, bend 51 may be proximate to electrodes 46A-46C, and the radius of curvature may be in the range of approximately 15 mm to 35 mm. In some examples, of the deflected tip of lead 30, for example, the portion of lead 30 between bend 51 and the distal end of lead 30 shown in FIG. 4B, may be in the range of approximately 5 mm to 40 mm, and more preferably approximately 7 mm to 20 mm, to allow suitable placement of lead 30 adjacent to a target nerve or nerves. In some examples, deflected tip of lead 30 may be deflected in the range of 10 degrees to 60 degrees from the major longitudinal axis of the lead 30, and more preferably approximately 35 degrees to 50 degrees, to allow suitable placement of lead 30 adjacent to a target nerve or nerves.

In certain examples, actuator 28 of housing 26 may be provided in different sizes and configurations to accommodate different sized hands and/or use of a right or left hand, either as ambidextrous or separate models.

Figure 5:
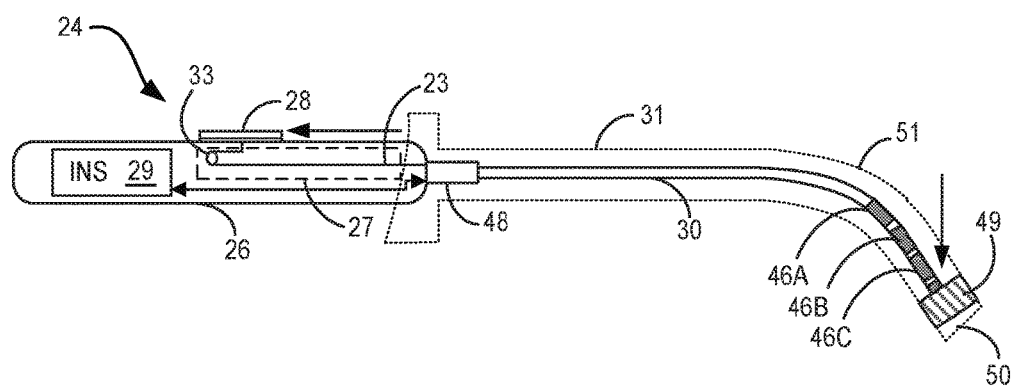
FIG. 5 is a view of an exemplary IMD like that shown in FIGS. 4A and 4B and additionally including a pulley.

FIG. 5 is a view of an exemplary IMD like that shown in FIGS. 4A and 4B and additionally including a pulley 33. Pull wire 23 may extend from the tip of lead 30 to a pulley 33 proximal to actuator 28 and then to actuator 28 such that that distal translation of actuator 28 with respect to housing 26 may result in increased tension on pull wire 23 and deflection of the tip of lead 30 and proximal translation of the actuator 28 with respect to housing 26 may result in reduced tension in pull wire 23 and straightening of the tip of lead 30.

Figure 6A:
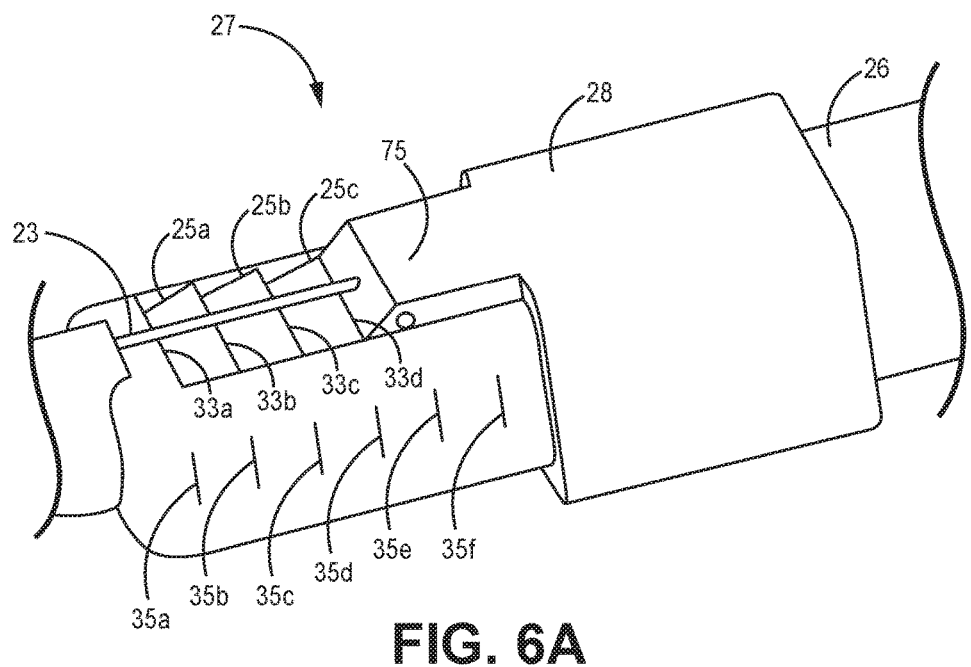
FIGS. 6A and 6B show perspective and cross-sectional views of an exemplary ratcheting system of the IMDs of FIGS. 1 and 4A-4C.
Figure 6B:
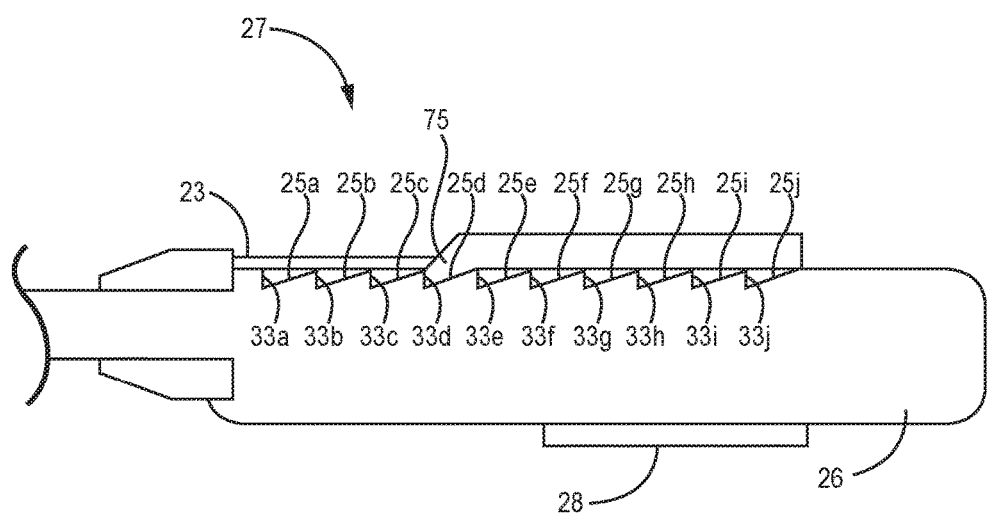

FIGS. 6A and 6B show perspective and cross-sectional views of an exemplary ratcheting system of the IMDs of FIGS. 1 and 4A-4C. The ratcheting system 27 may include a linear rack of teeth 25 and a spring-loaded pawl 75, coupled to or a part of actuator 28, that engages with the 25 teeth.

Actuator 28 may be coupled to or comprise the pawl 75 and the pawl 75 may engage with the teeth 25 of ratchet system 27 at a plurality of positions along a thumb (or finger) slide. Each position between a pair of teeth 25 may receive the pawl 75 of actuator 28 to engage the actuator 28 at a corresponding position along the slide.

The teeth 25 of the may be asymmetrical to allow for the pawl 75 to advance over the teeth 25 in one direction but not the other and thus allow movement of actuator 28 in one direction and not the other. As shown, pawl 75 is engaged between teeth 25c and 25d such that it is retained by wall 33d of tooth 25c to prevent movement of pawl 75 in a distal direction.

When the pawl 75 of actuator 28 is engaged with a particular position between a pair of teeth 25, sufficient force may need to be applied to actuator 28 to release the pawl 75 of the actuator 28 from the position and past the next tooth 25 to advance the actuator 28. Each position between a pair of adjacent teeth 25 may correspond to a different deflection angle of the tip of lead 30.

Housing 26 may also include markers 35 along side ratchet system 27 such that advancement of actuator 28 to a new position results in placement of actuator 28 next to a corresponding marker 35, providing visual feedback to the physician. Although markers 35 are shown as simple lines, markers 35 may include alternative or additional information including, for example, a deflection angle associated with the portion for the respective marker 35.

In some examples, ratchet system 27 may include a trigger system that may engage with the pawl 75 to release the pawl 75 from engagement with the teeth 25 such that actuator 28 may move in either a proximal or distal direction. In some examples, the trigger system may engage with the rack of teeth 25 to displace the rack from engagement with the pawl 75 to allow for movement of actuator 28 in either a proximal or distal direction.

In some examples, a locking mechanism may include one or more springs for maintaining the pawl 75 in a particular position, and thus locking the pawl 75, the actuator 28, and the distal portion of lead 30 in place, and/or for allowing the pawl 75 to advance to different positions and thus unlocking the pawl 75, actuator 28, and the distal portion.

Figure 7:
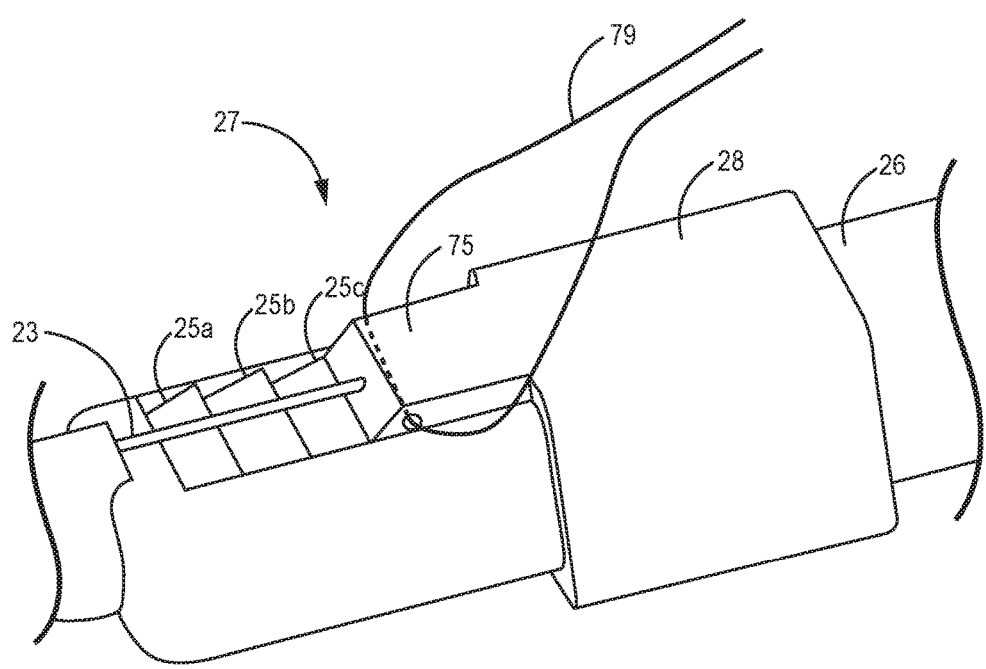
FIG. 7 shows a perspective view of another exemplary ratcheting system of the IMDs of FIGS. 1 and 4A-6A.

FIG. 7 shows a perspective view of another exemplary ratcheting system of the IMDs of FIGS. 1 and 4A-6B. As described with respect to FIGS. 6A and 6B, the ratcheting system 27 may include a linear rack of teeth 25 and a spring-loaded pawl 75, coupled to or a part of actuator 28, that engages with the 25 teeth. A suture 79 may be used to release pawl 75 from the teeth 25 such that pawl 75 may be moved in a proximal direction. In some examples, suture 79 may be used to release pawl 75 from the teeth 25 such that pawl 75 may be moved in a distal direction, according to particular needs. Suture 35 may pass through a lumen in pawl 75 or may otherwise be temporarily or permanently coupled to pawl 75. In some examples, suture 79 may be coupled to pawl 75 when needed and removed when not needed.

Figure 8:
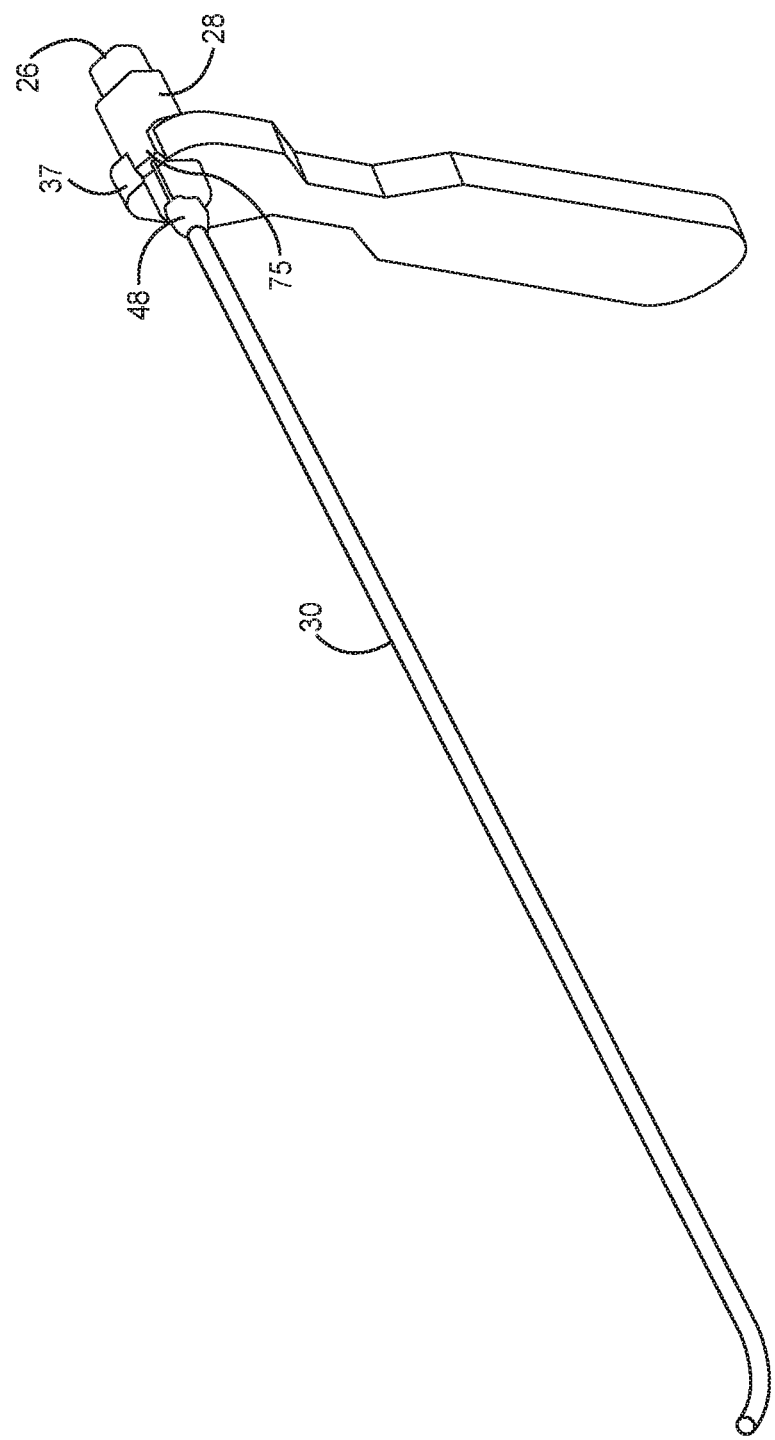
FIG. 8 shows a perspective view of an exemplary IMD like that shown in FIGS. 1 and 4A-7 and additionally including a tool for holding an actuator, which may be in the form of a collar, of the IMD in place.

FIG. 8 shows a perspective view of an exemplary IMD like that shown in FIGS. 1 and 4A-7 and additionally including a tool 37 for holding the actuator 28, which may be in the form of a collar, of the IMD in place. Tool 37 may be used to hold the device in place and capture the actuator 28, thus allowing a practitioner to push on the proximal end of the housing 26 to pull the pull-wire with respect to the housing 26 and generate (and/or lock) deflection of the lead 30.

In some examples, a practitioner may grasp the tool 37 with the practitioner's fingers and may push on the proximal end of the housing 26 with the practitioner's thumb.

Figure 9:
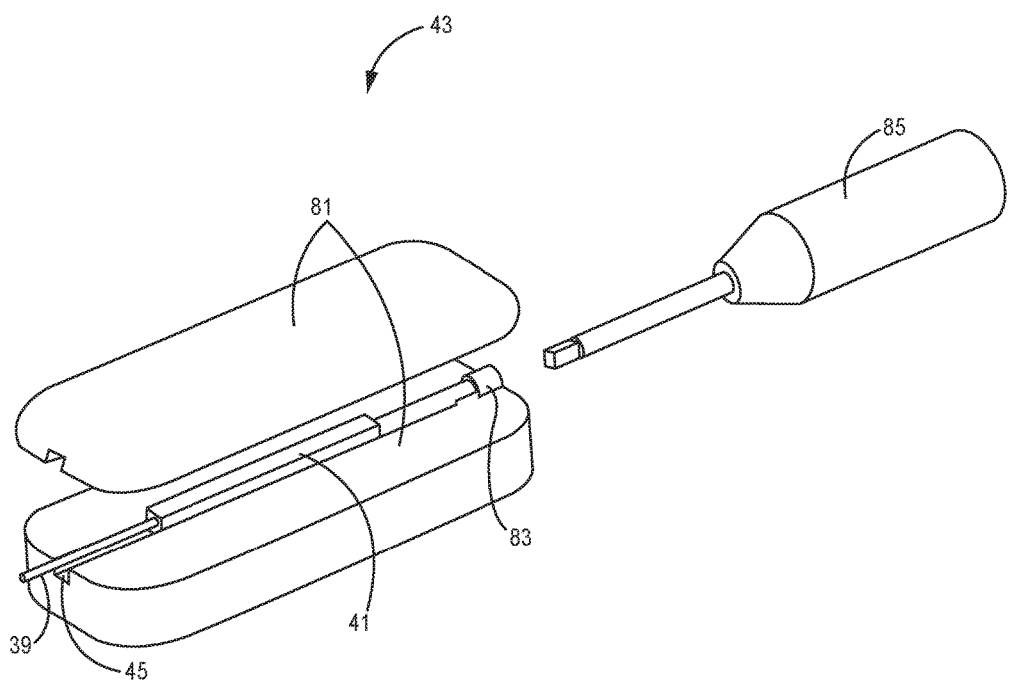
FIG. 9 shows a perspective view of an additional exemplary ratcheting system of the IMD of FIG. 1.

FIG. 9 shows a perspective view of an additional exemplary ratcheting system 43 of the IMD of FIG. 1. Housing 81 of the IMD may include a set screw 83 engaged with a rectangular key 41 that may be in a slotted keyway 45 of the housing 81. The rectangular key 41 may be attached to the pull-wire 39. A tool 85 may be used to rotate the set screw 83. Rotation of the set screw 83 may move the key 41 in a proximal or distal direction and thus increase of decrease tension on the pull wire 39 and deflect or straighten the lead.

Figure 10A:
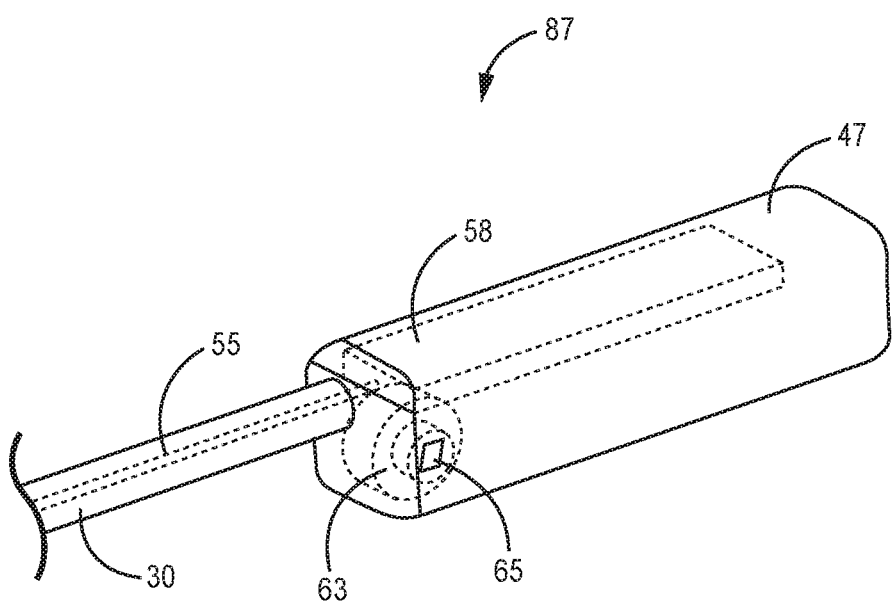
FIGS. 10A-10C show perspective and side cross-sectional views of an additional exemplary ratcheting system of the IMD of FIG. 1.
Figure 10B:
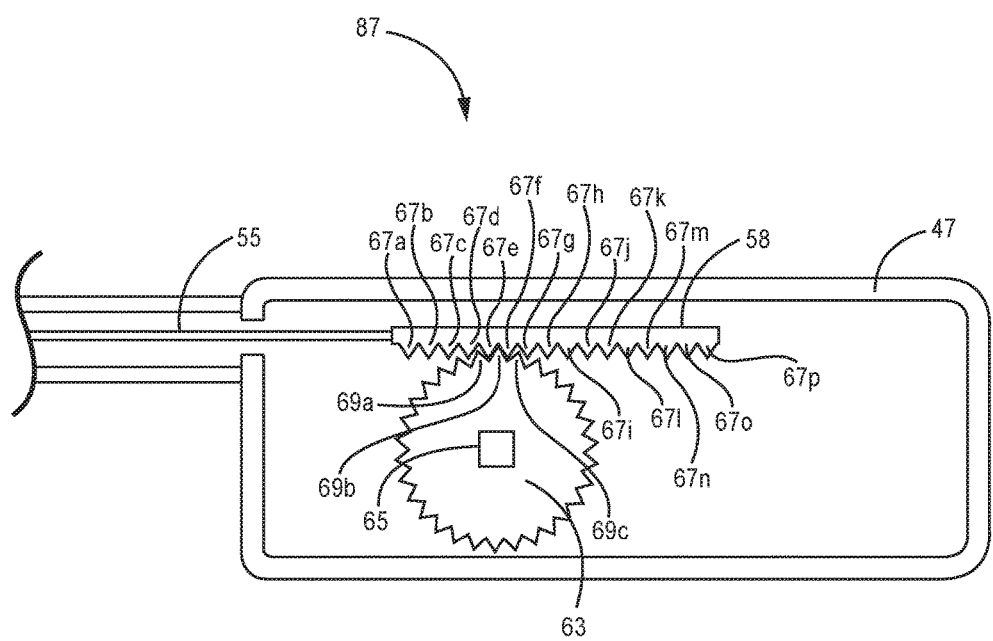
Figure 10C:
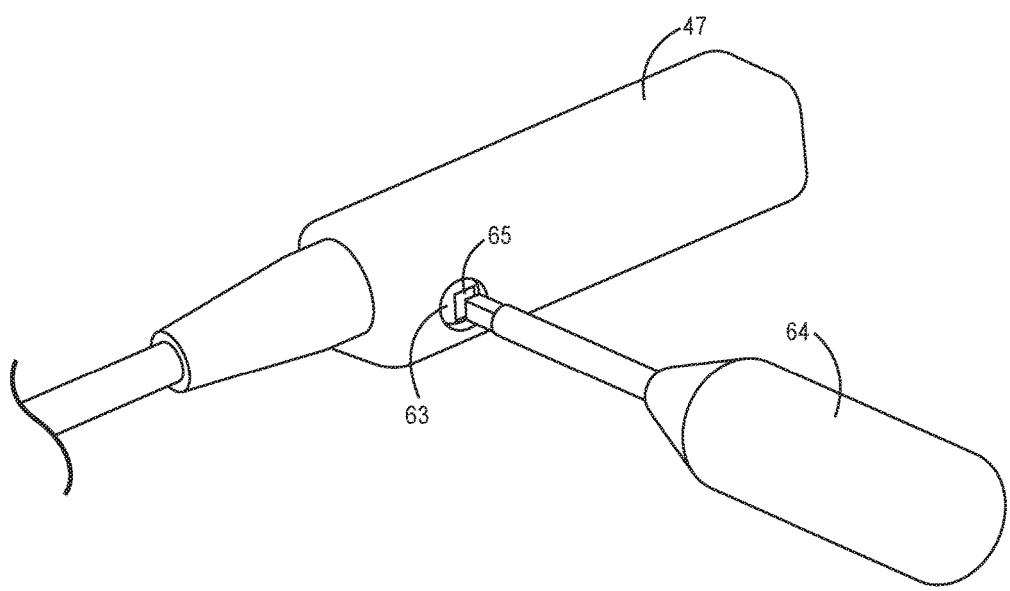

FIGS. 10A, 10B, and 10C show perspective and side cross-sectional views of an additional exemplary ratcheting system 87 of the IMD of FIG. 1. A gear 63 may include a plurality of teeth 69 that may engage with a rack 58 of teeth 67. The rack 58 may be coupled to pull-wire 55. The gear 63 and rack 58 may be within housing 47. When rotated, the gear 63 may displace the rack 58, thus displacing the pull-wire 55 and causing deflection or straightening of the lead. The gear 63 may include a recess 65 with which a tool 64 may be configured to engage such that rotation of the tool 64 may result in rotation of the gear 63 and deflection or straightening of the lead.

Figure 11A:
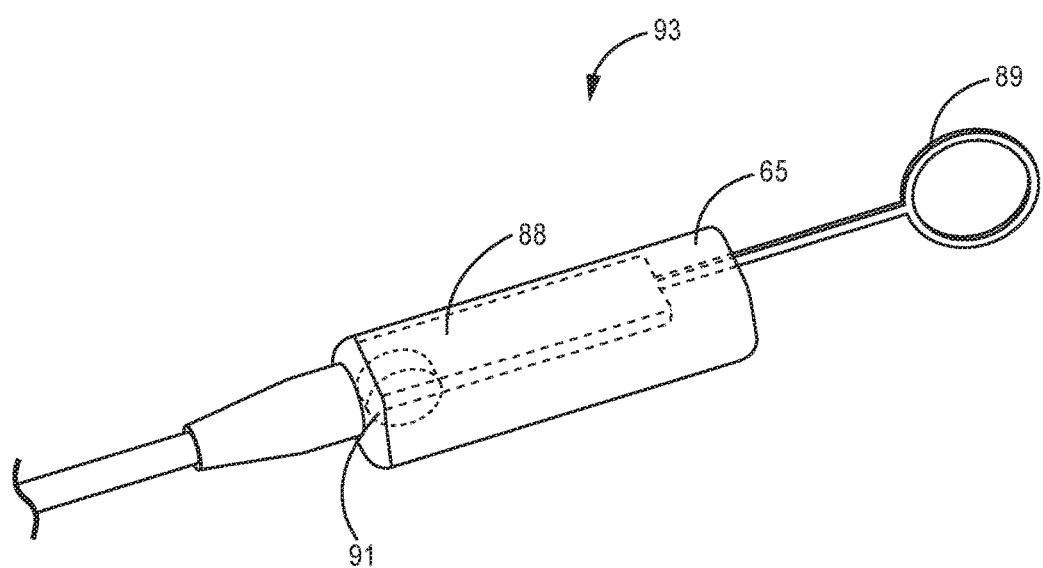
FIGS. 11A and 11B show perspective and side cross-sectional views of an additional exemplary ratcheting system of the IMD of FIG. 1.
Figure 11B:
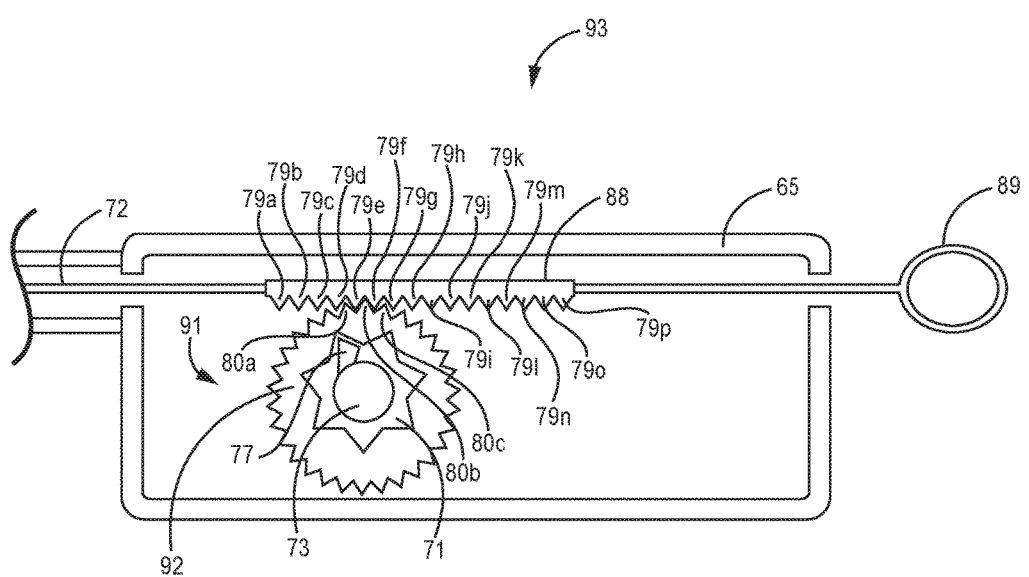

FIGS. 11A and 11B show perspective and side cross-sectional views of an additional exemplary ratcheting system 93 of the IMD of FIG. 1. Similar to the ratcheting system 87 of FIGS. 10A-10C, a gear 92 may include a plurality of teeth 80 that may engage with a rack 88 of teeth 79. The gear 63 and rack 58 may be within housing 65. The rack 88 may be coupled to pull-wire 72 and to a pull ring 89. A practitioner may displace the pull-ring 89 in a proximal direction with respect to the housing 47 to displace the rack 88 in the proximal direction with respect to the housing 65 and increase tension on the pull-wire 72, causing deflection of the lead The gear 92 may be a part of a gear assembly 91 further including an inner rod 73 about which the gear 92 rotates. The inner rod 73 may include a pawl 77 and the gear 92 may include a recess 71. The pawl 77 may be configured to engage with the recess 71 to allow rotation of the gear 92 in one direction but not the other. For example, in the illustrated example, the recess 71 and pawl 77 may engage to allow rotation of the gear 92 that allows for proximal movement of the rack 88 but not distal movement of the rack 88. This may allow for deflection of the lead but prevent straightening of the lead when it has been deflected. In some examples, the gear assembly 91 may be configured such that, if desired, a practitioner may release the pawl 77 from engagement with the recess 71 but such disengagement may require action on the part of the practitioner. In this way, unintended straightening of the lead may be prevented.

Figure 12A:
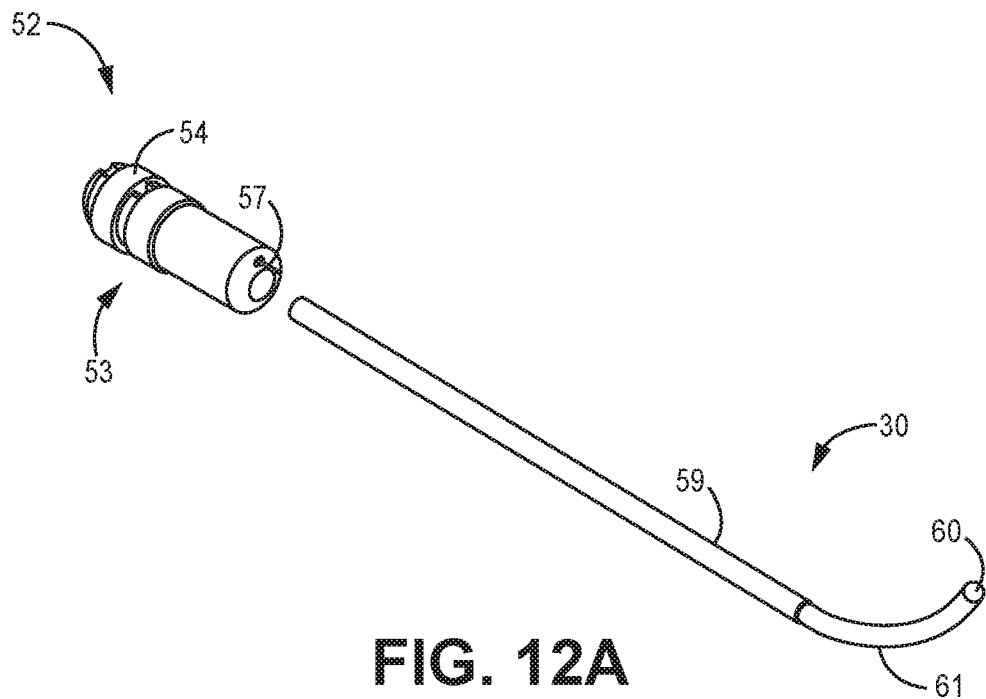
FIGS. 12A-12E show views of another exemplary IMD with the lead having a deflecting tip and a rotating actuator configured to cause the tip to deflect to implant the electrical lead adjacent to a sacral nerve.

FIGS. 12A-12E show views of another exemplary IMD 52 with lead 30 having deflecting tip 60 and a rotating actuator configured to cause the tip 60 to deflect to implant electrical lead 30 adjacent to a sacral nerve. FIG. 12A illustrates an internal view of IMD 52. In the example of FIG. 12A, IMD 52 includes housing 53, keyed pull ring 54, pull-wire 57, lead 30, shielding 59, tip 60, and bend 61. Although not shown in FIG. 12A-12E, IMD 52 may be implanted using an introducer, such as introducer 31 as described in FIGS. 4A and 4B.

Figure 12B:
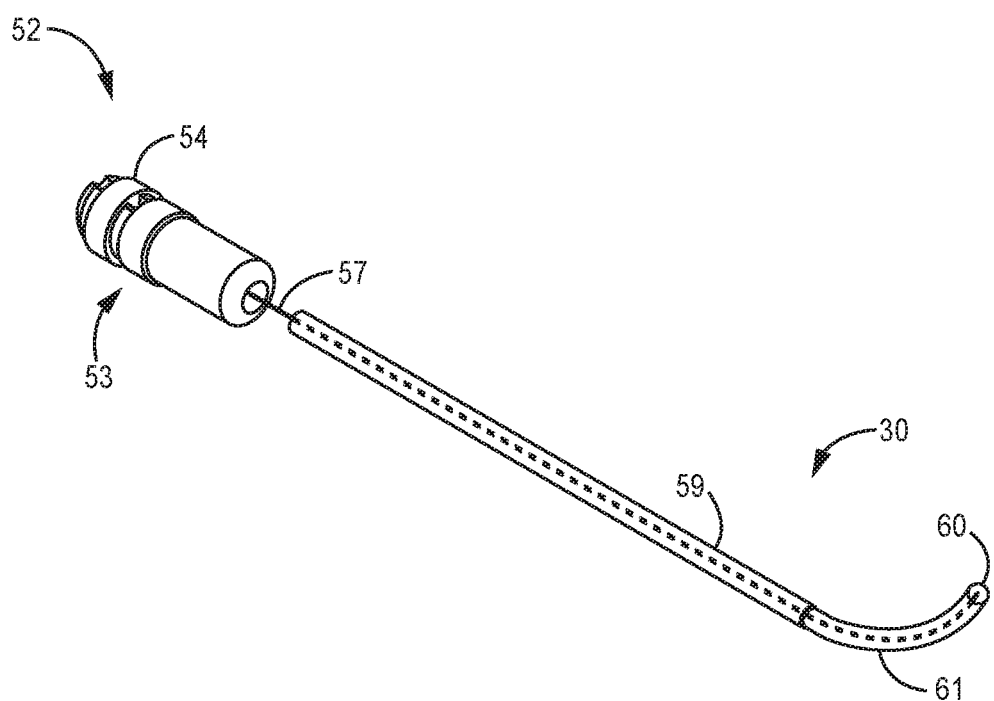

Housing 53 may be substantially cylindrical in shape and may include keyed pull ring 54 that is attached to pull-wire 57. As shown in FIG. 12B, pull-wire 57 may extend along the body of lead 30 and/or may extend within housing 53. In the example of FIGS. 12A, 12B, 12C, 12D and 12E lead 30 may be deflected with deflection actuator 62 with resistance from shielding 59 to form a curved shape about bend 61 to facilitate entry through sacral foramen 20 and enable access to sacral S3 nerve 38. In some examples, shielding 59 may be magnetic resonance imaging (MM) shielding (e.g., an MIll braid), which may be stiffer than tip 60 of lead 30. Housing 53 may house an INS (e.g., INS 29 as described in with reference to FIGS. 1, 4A, and 4B).

A tip of an introducer may be used to pierce tissue and create a tunnel through pelvis 10. Lead 30 covered by the introducer may be inserted into the patient and twisted about a long axis of housing 53 to pass through sacral foramen 20. In some examples, a physician may deflect tip 60 of lead 30 within the introducer to facilitate accurate placement of lead 30 adjacent sacral S3 nerve 38.

In some examples, a section may be formed near or on the tip of the introducer, e.g., by any of the techniques described with respect to section 49 as described in FIGS. 4A and 4B, to provide for test stimulation during placement of lead 30. In these examples, the section may be cylindrical, circular, or rectangular in shape. In some examples, the introducer covering lead 30 may be hollow and open near tip 60, e.g., to permit introduction of a fluid into the interior of pelvis 10.

In some examples, housing 53 may be cylindrical, spherical, or another ergonomic shape designed to be held by one hand. A cylindrical housing 53 shape may provide flexibility to a physician using IMD 52. The physician may hold housing 53 at any point about the circumference of cylindrical housing 53 to direct lead 30 to any location. A cylindrical housing shape may also allow the physician to easily rotate and manipulate IMD 52 when attempting to position lead 30 near sacral S3 nerve 38.

Similar in size to housing 26 discussed above with reference to FIGS. 4A and 4B, housing 53 may generally be in a range of approximately 10 mm to 30 mm in length, and 0.5 mm to 10 mm in diameter. In some examples, housing 53 may be in a range of approximately 10 mm to 15 mm in length, 2 mm to 4 mm in width, and 1 mm to 3 mm in thickness. Housing 53 may be provided in different sizes to accommodate both an INS (e.g., INS 29 as described in FIGS. 4A and 4B) and different sized hands of varying physicians.

Housing 53 may be constructed of materials similar to those described with reference to housing 26 as described in FIGS. 4A and 4B. In some examples, a plastic material may be used to construct lead 30, which include an electrical conductor for delivery of stimulation energy to one or more electrodes (not shown) at or near distal tip 60.

Lead 30 may include conductors coupling one or more electrodes on lead 30 to contacts at or near a proximal end of lead 30 and the contacts may be coupled to electrical circuit terminals of INS 29 to allow supply of electrical energy from INS 29 to the one or more electrodes of lead 30.

Figure 12C:
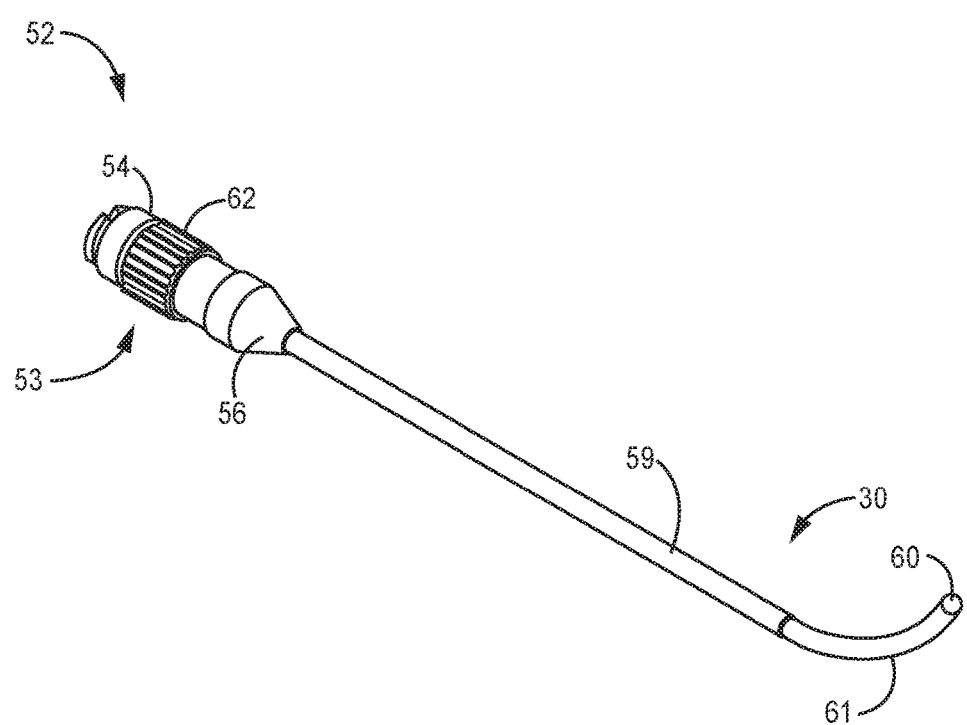
Figure 12D:
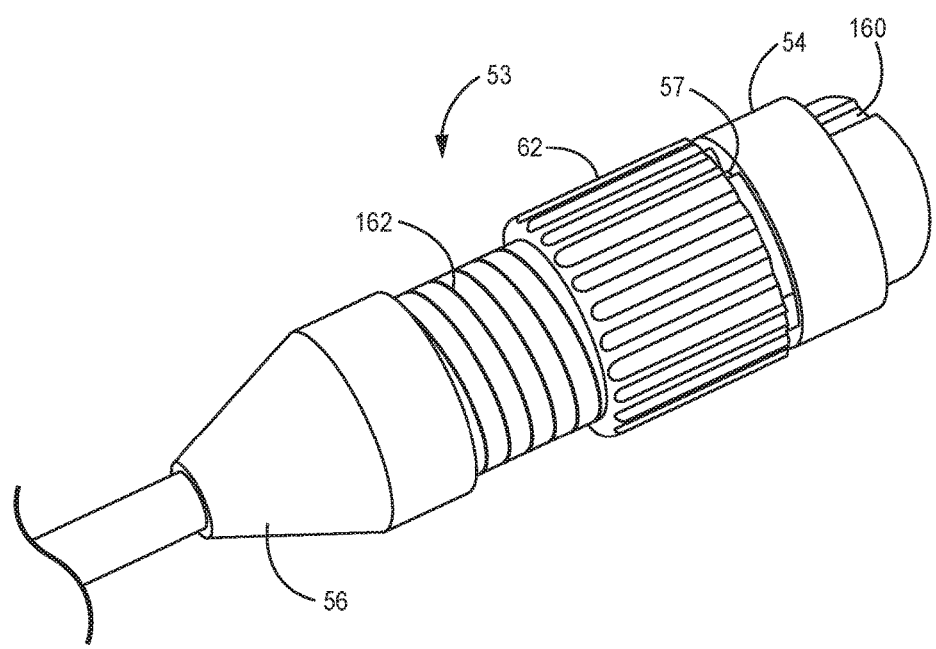

FIG. 12C illustrates an external view of IMD 52. FIG. 12D illustrates an external view of a portion of IMD 52. In the example of FIGS. 12C and 12D, IMD 52 also includes neck 56 and deflection actuator 62. In some examples, neck 56 securely attaches lead 30 to housing 53. In some examples, neck 56 provides strain relief between lead 30 and housing 53. In some examples, neck 56 provides a seal between housing 53 and lead 30.

In some examples, deflection actuator 62 may be provided on housing 53 to facilitate deflection of the distal end of lead 30 by a physician. For example, deflection actuator 62 may be a knurled knob with internal threads that can be turned to increase tension on pull-wire 57. In this example, housing 53 may have external threads 162 that are configured to engage with the internal threads of deflection actuator 62 such that rotation of deflection actuator 62 may result in translation of deflection actuator 62 with respect to housing 53. Keyed pull ring 54 may be part of deflection actuator 62 or may be positioned next to deflection actuator 62 or may otherwise receive force from deflection actuator 62 such that translation of the deflection actuator 62 with respect to housing 53 and lead 30 may result in translation of keyed pull ring 54 with respect to housing 53 and lead 30. Because keyed pull ring 54 may be connected to pull-wire 57, translation of keyed pull ring 54 away from tip 60 of lead 30 may increase tension on pull-wire 57 and result in deflection of tip 60. Keyed pull ring 54 may include a keyed component that may fit within a slot of housing 53 to prevent rotation of keyed pull ring 54 about housing 53 so that movement of keyed pull ring 54 with respect to housing 53 is limited to translation with respect to housing 53. In certain embodiments, pull wire 57 may extend substantially from the tip of lead 30 to keyed pull ring 54 such that proximal translation of keyed pull ring 54 with respect to housing 53 may result in increased tension on pull wire 57 and deflection of the tip of lead 30 and distal translation of the keyed pull ring 54 with respect to housing 53 may result in reduced tension in pull wire 57 and straightening of the tip of lead 30. In certain examples, pull wire 57 may extend from the tip of lead 30 to a pulley mechanism proximal to keyed pull ring 54 and then to keyed pull ring 54 such that that distal translation of keyed pull ring 54 with respect to housing 53 may result in increased tension on pull wire 57 and deflection of the tip of lead 30 and proximal translation of the keyed pull ring 54 with respect to housing 53 may result in reduced tension in pull wire 57 and straightening of the tip of lead 30.

Deflection actuator 62 may employ a ratcheting system similar to ratcheting system 27 described with reference to FIG. 1. For example, keyed pull ring 54 may include or be coupled to a spring-loaded pawl. For example, the keyed portion of key pull ring 54 may include a pawl and the slot of housing 53 may include a track of teeth configured to engage with the pawl and allow for incremental movement of the key pull ring 54, provide for suitable resistance to movement to prevent accidental movement, provide for tactile, auditory, and/or visual feedback for the physician, and may prevent movement in an opposite direction. The ratchet system may also include a trigger system that may engage the pawl to release it from engagement with the track and allow for movement in both directions to allow for straightening, or decreased deflection, of the lead 30. The ratchet system may include a trigger system that may displace the track from displace the track from engagement with the pawl and allow for movement of the keyed pull ring in both directions and straightening or reduced deflection of the lead 30.

Figure 12E:
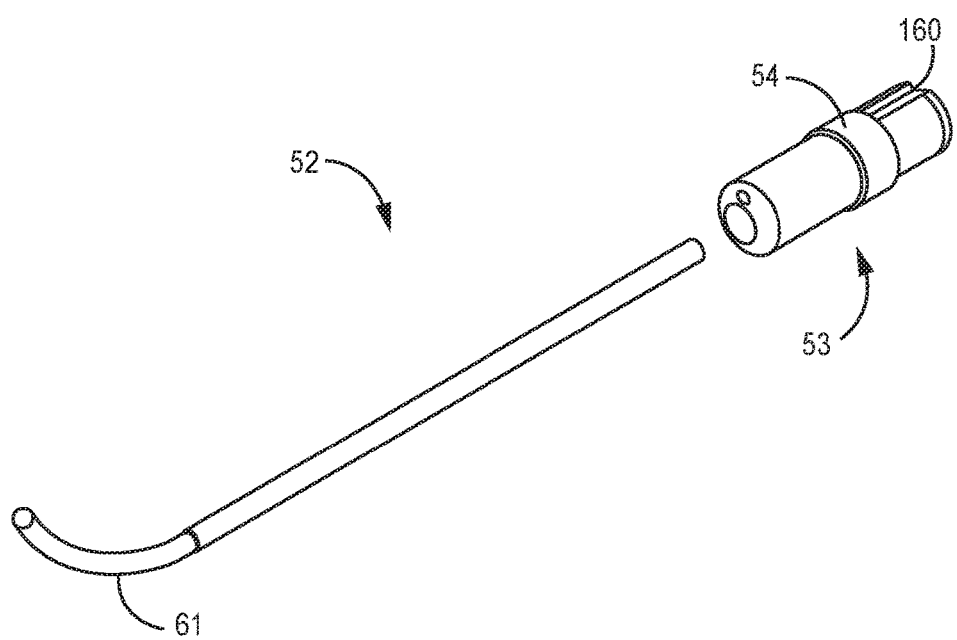

FIG. 12E illustrates an internal view of IMD 52 showing keyed pull ring 54 which may include a keyed portion (not shown) fitting within slot 160 of housing 53, as described above with reference to FIGS. 12C and 12D.

In operation, in some examples, a physician may penetrate a sacral foramen with a distal tip of an introducer and rotate deflection actuator 62 on housing 53 to deflect tip 60 of lead 30. In these examples, the physician may move lead 30 into the interior of the pelvis such that distal tip 60 is placed adjacent to a desired nerve site (e.g., the sacral nerve). In some examples, deflection actuator 62 may also be translated to lock the deflection caused by deflection actuator 62. For example, keyed pull ring 54 may be translated into a detent that prevents translational movement of keyed pull ring 54 and thus prevents straightening or deflection of the tip of lead 30. Conversely, in other examples, deflection actuator 62 may be translated to deflect distal tip 60 of lead 30 and rotated to lock the deflection caused by deflection actuator 62. For example, the keyed pull ring 54 may be rotated such that the keyed portion is rotated into a groove perpendicular to slot 160 so that the keyed portion is no longer in the slot and the groove acts as a stop for keyed pull ring 54 to prevent distal or proximal translation of keyed pull ring 54, thus preventing straightening or additional deflection of the tip of lead 30.

In some examples, after locking deflection actuator 62, the physician may remove the introducer from the patient and implant IMD 52 into the patient. Additionally, in some examples, after implantation of cylindrical IMD 52, the physician may later remove the implanted IMD 52 from the patient and unlock deflection actuator 62 in order to change the deflection of distal tip 60 of lead 30. In these examples, the change in the deflection of distal tip 60 of lead 30 may result in better placement of lead 30 near the sacral nerve.

Although particular types of actuator configurations have been described with reference to FIGS. 4A-12E, other suitable actuator configurations may be used according to particular needs. For example, an actuator may be in the form of a thumbwheel configuration that may transfer rotation of the thumbwheel to translation of a pull-wire, such as pull-wire 57, with respect to tip of a lead, such as lead 30, to cause displacement of the tip of the lead. Such a configuration may include a pinion gear or worm gear for translating the rotation of a thumbwheel to a translation of a member, such as a rack or worm gear, coupled to the pull-wire.

Figure 13:
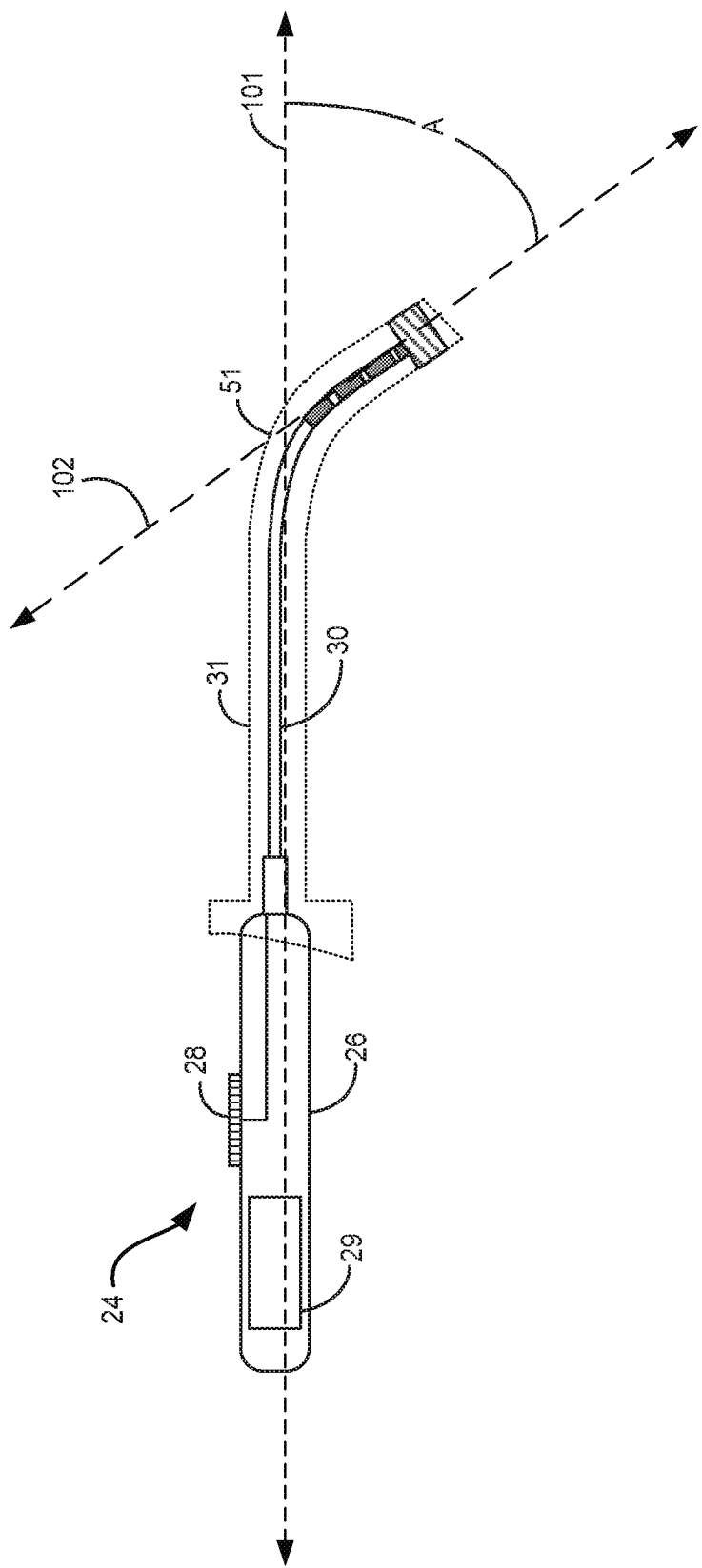
FIG. 13 shows a view of an exemplary IMD with a lead having a deflected tip.

FIG. 13 shows a view of an exemplary IMD 24 with lead 30 having a deflected tip. IMD 24 may include housing 26 comprising INS 29 and actuator 28 coupled to lead 30 and introducer 31 at least partially surrounding lead 30. Lead 30 may be deflected at bend 51. A first portion of lead proximal to bend 51 may extend substantially along a first axis 101. A second, deflected portion of lead 30 distal to bend 51 may extend substantially along a second axis 102. The angle "A" formed between the first axis and the second axis may be in the range of 10 degrees to 60 degrees, according to particular needs. Although lead 30 is shown to be deflected away from a side of IMD 24 having actuator 28, lead 30 may be configured to deflect in any suitable direction according to particular needs.

Figure 14A:
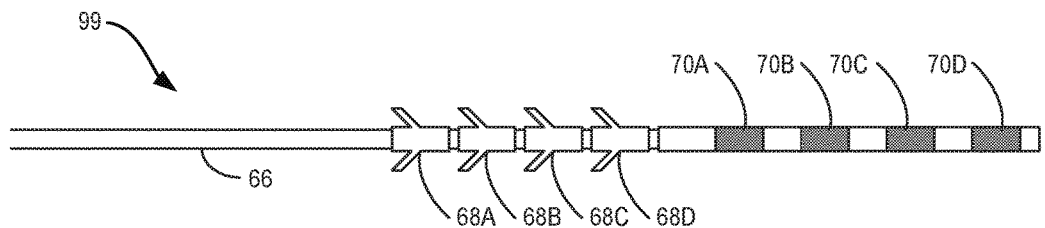
FIGS. 14A-14C are conceptual diagrams illustrating exemplary electrical leads with deflecting tips useful in the examples of FIGS. 1-13 and further including tines to secure the lead within a patient.
Figure 14B:
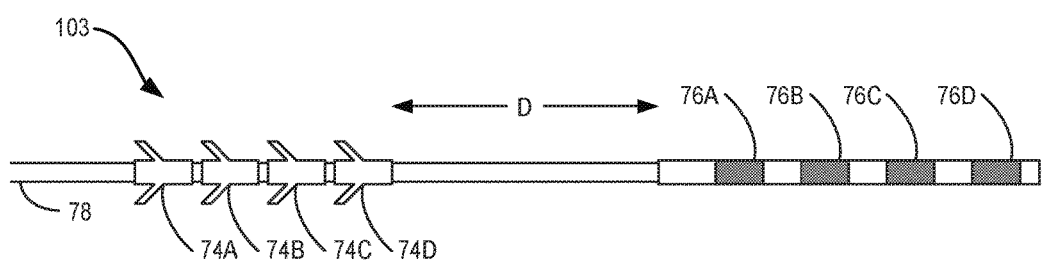
Figure 14C:
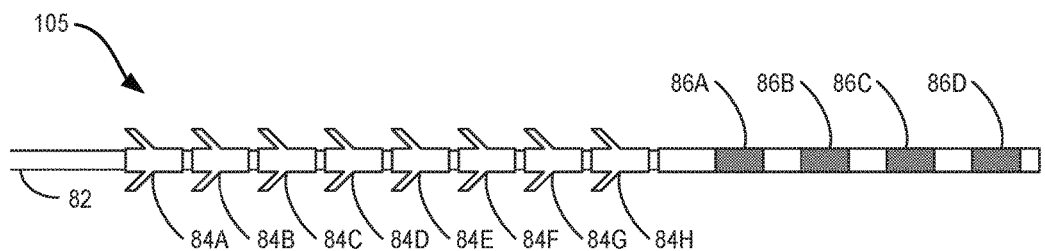

FIGS. 14A-14C are conceptual diagrams illustrating exemplary electrical leads with deflecting tips useful in the examples of FIGS. 1-13 and further including tines to secure the lead within a patient.

As shown in FIG. 14A, lead 99 includes housing 66, tines 68A, 68B, 68C, and 68D (collectively tines 68), and electrodes 70A, 70B, 70C, and 70D (collectively electrodes 70). Lead 99 may be a standard lead that includes all four tines 68 close to electrodes 70. Implanting lead 30 may be beneficial due to tines 68 being anchored close to electrodes 70. A smaller distance between tines 68 and electrodes 70 may allow less movement of electrodes 70 with respect to adjacent sacral S3 nerve 38.

Electrodes 70 may be more effective in delivering electrical stimulation when the electrodes are located close to sacral S3 nerve 38. If electrodes 70 migrate away from sacral S3 nerve 38, efficacy of stimulation therapy may decrease. Therefore, tines 68 located close to electrodes 70 may be beneficial to therapy efficacy. However, tines 68 may not be capable of anchoring into a solid tissue if they are located too close to electrodes 70.

FIG. 14B illustrates a lead 103 which includes housing 78, tines 74A, 74B, 74C, and 74D (collectively tines 74), and electrodes 76A, 76B, 76C, and 76D (collectively electrodes 76). Tines 74 are located a distance D away from the most proximal electrodes 76. Lead 103 may be capable of anchoring tines 74 in a muscle while enabling electrodes 76 to reach further away from the anchoring point to sacral S3 nerve 38. Distance D may be generally in a range of approximately 0.5 mm to 10 mm, and more preferably 1 mm to 4 mm. While lead 103 may provide a more secure anchoring point, electrodes 76 may be free to migrate to an unacceptable distance away from sacral S3 nerve 38.

FIG. 14C illustrates a lead 105 which includes housing 82, tines 84A, 84B, 84C, 84D, 84E, 84F, 84G, and 84H (collectively tines 84), and electrodes 86A, 86B, 86C, and 86D (collectively electrodes 86). The increased number of tines 84 located on lead 30 may provide secure anchoring in a muscle and soft tissue closer to sacral S3 nerve 38. Lead 105 may be capable of providing better anchoring points and eliminating migration of electrodes 86 with respect to sacral S3 nerve 38. However, removal of lead 105 may injure a greater volume of tissue. Therefore, lead 105 may be more appropriate for patients with more active lifestyles where lead migration may be a problem.

In any of lead of FIGS. 14A-14C, any number of electrodes or tines may be implemented. Although the lead includes four electrodes in each of the examples illustrated in FIGS. 14A-14C, a lead may include one, two, four, eight or more electrodes. In addition, any number of tines may be used. Also, in some cases, it may be desirable to deploy two or more leads, each carrying one or more electrodes. Any of these configurations may be possible and desirable when implanting a lead to stimulate sacral S3 nerve 38 via the approach described in this disclosure.

In certain examples, tines may be flexible and may fold, toward a lead, to assume a low profile around the lead when introducer 31 is surrounding the lead and may unfold to positions extending substantially radially from the lead, as illustrated in FIGS. 14A-14C, when introducer 31 is removed.

The tines illustrated in these examples may be used in combination with any suitable lead deflection mechanism described herein.

Figure 15:
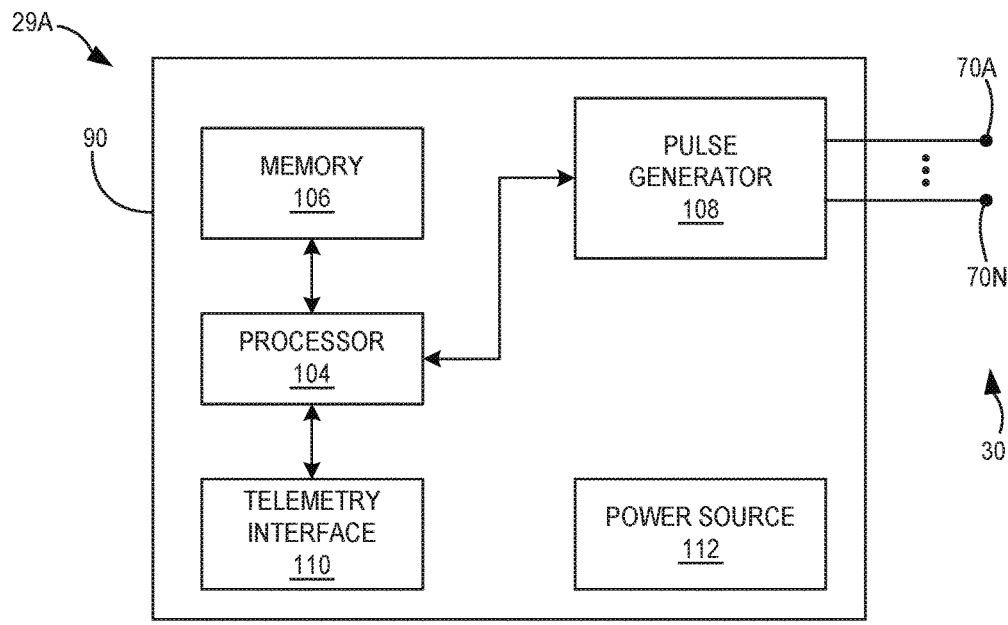
FIGS. 15 and 16 are block diagrams illustrating exemplary electrical stimulators configured for use with a lead with a deflecting tip in an IMD useful in the examples of FIGS. 1-14C.
Figure 16:
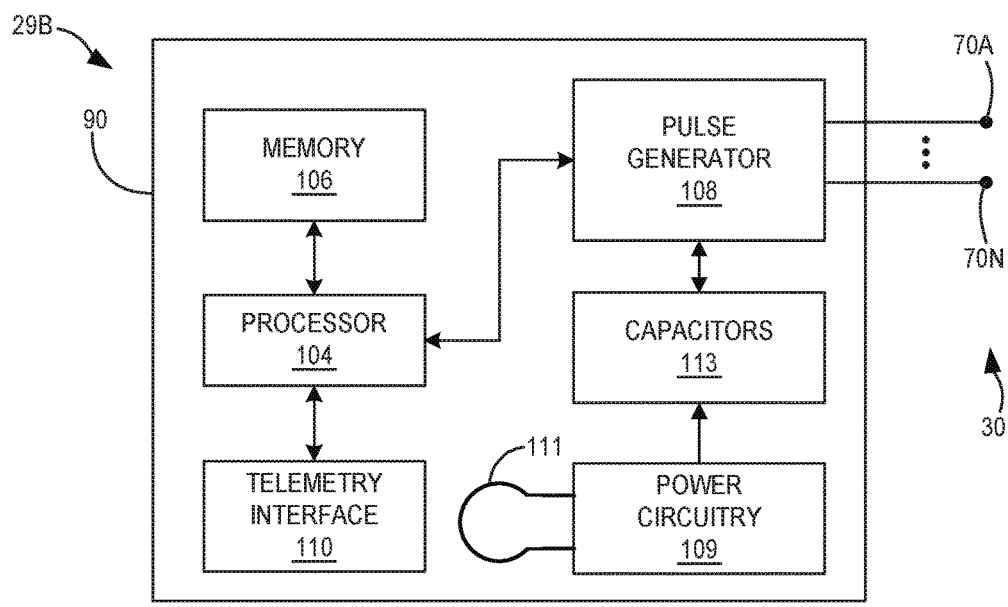

FIGS. 15 and 16 are block diagrams illustrating exemplary electrical stimulators, INS devices 29A and 29B, configured for use with a lead with a deflecting tip in an IMD useful in the examples of FIGS. 1-14C. Components of INS devices 29A and 29B may be within housing 90 of an IMD (e.g., similar to housing 26 of IMD 24 or housing 53 of IMD 52). Components within housing 90 include processor 104, memory 106, pulse generator 108, and telemetry interface 110. In other examples, housing 90 of INS devices 29A and 29B may include a greater or fewer number of components. In some examples, INS device 29A may be an active INS device having power source 112, which may include a battery. By contrast, in some examples, INS device 29B may be a passive INS device having power circuitry 109 and capacitors 113 and may not include a battery. Power circuitry 109 and capacitors 113 may be charged by an external programmer. In other examples, an INS device may include both active and passive components, such that an INS device may include power circuitry 109 and capacitors 113 in addition to power source 112.

In some examples, processor 104 may include one or more processors configured to perform the operations needed to generate and deliver test and therapy stimulation signals to the patient. In various examples, INS devices 29A and 29B may include one or more processors 104 or other control hardware within housing 90, such as one or more microprocessors, digital signal processors (DSPs), application specific integrated circuits (ASICs), field programmable gate arrays (FPGAs), or any other equivalent integrated or discrete logic circuitry, as well as any combinations of such components.

Memory 106 stores instructions for execution by processor 104, stimulation parameters and, optionally, information related to the use of lead 30. Memory 106 may include separate memories for storing instructions, stimulation parameter sets, and stimulation information, or a common memory. In some examples, memory 106 may be random access memory (RAM), read only memory (ROM), programmable read only memory (PROM), erasable programmable read only memory (EPROM), electronically erasable programmable read only memory (EEPROM), flash memory, comprising executable instructions for causing the one or more processors to perform the actions attributed to them.

In some examples, pulse generator 108 may be programmed with stimulation pulse parameters appropriate for delivery of test stimulation in the form of stimulation pulses delivered continuously or in selected bursts via one or more of electrodes 70A-70N on lead 30. Additionally, in some examples, pulse generator 108 may be a trial or chronic stimulator used to treat the patient, such that pulse generator 108 may also be programmed with stimulation pulse parameters appropriate for delivery of stimulation therapy via electrodes 70A-70N on lead 30. In some examples, electrodes 70A-70N on lead 30 may correspond to the one or more electrodes on lead 30 as described in FIGS. 3-5.

Processor 104 controls pulse generator 108 to deliver electrical stimulation therapy via electrodes 70A-70N on lead 30. Based on stimulation parameters programmed by the physician through telemetry interface 110, processor 104 instructs appropriate stimulation by pulse generator 108. Information may also be received from telemetry interface 110 at any time during operation, in which case a change in stimulation parameters may immediately occur. In some examples, telemetry interface 110 may include a user interface that can be accessed directly, before implantation of housing 90, as a set of switches, dials, buttons, and/or other input media. In some examples, telemetry interface 100 may include a user interface that may accessed, before and/or after implantation of housing 90, via an external programmer that transmits information to INS device 29A or 29B by telemetry interface 110 using any known wired or wireless telemetry. For example, wireless telemetry of telemetry interface 110 in INS devices 29A and 29B may be accomplished by radio frequency (RF) communication, Bluetooth, Near-Field Communication (NFC), or a proximal inductive interaction of INS devices 29A and 29B with another programming device via telemetry interface 110. Processor 104 may control telemetry interface 110 to exchange information with the programming device. Processor 104 may transmit operational information and other information to the programming device via telemetry interface 110.

Processor 104 may determine any pulse parameter adjustments based on the received information, and may load the adjustments into memory 106 for use during delivery of stimulation. As mentioned above, the user interface may include a series of switches, dials, or buttons for changing stimulation parameters. The user interface may also include an LED or LCD display indicating the values of current stimulation parameters, battery life, and any operational information. As mentioned above, the user interface may be provided by an external programmer that may be separate from IMB 24 and used to wirelessly control INS devices 29A or 29B before, during, and/or after implantation.

In the example of FIG. 15, power source 112 may deliver operating power to the components of INS device 29A. Power source 112 may include a battery and a power generation circuit to produce the operating power. In some examples, the battery may be rechargeable to allow extended operation. Recharging may be accomplished through proximal inductive interaction between an external charger and an inductive charging coil.

In the example of FIG. 16, INS device 29B may be a passive INS device that includes power circuitry 109 with coil 111 and capacitors 113 instead of a battery or other power storage device. Additional information regarding, for example, a passive INS device including power circuitry may be found in U.S. Patent Application Publication No. US20130110201 A1, filed May 2, 2013, entitled "Medical Devices for Trial Stimulation," the entire contents of which being incorporated herein by reference. Alternatively or in addition, the components described herein may be powered by other suitable mechanisms. For example, any of the devices described herein may be powered by transmission of acoustic energy (ultrasound).

In some examples, an INS device may include the power components of both INS devices 29A and 29B. In these examples, the INS device may be an active INS device prior to implantation to confirm the location of electrodes 70A-70N on lead 30 are located adjacent to the sacral nerve and a passive INS device after implantation. In this way, power source 112 of the INS device may be limited to only allow for location of lead 30 adjacent to the target nerve, whereas power circuitry 109 with coil 111 and capacitors 113 may be not be limited in the same way as power source 112 and instead may be used to provide chronic and trial stimulation.

Figure 17:
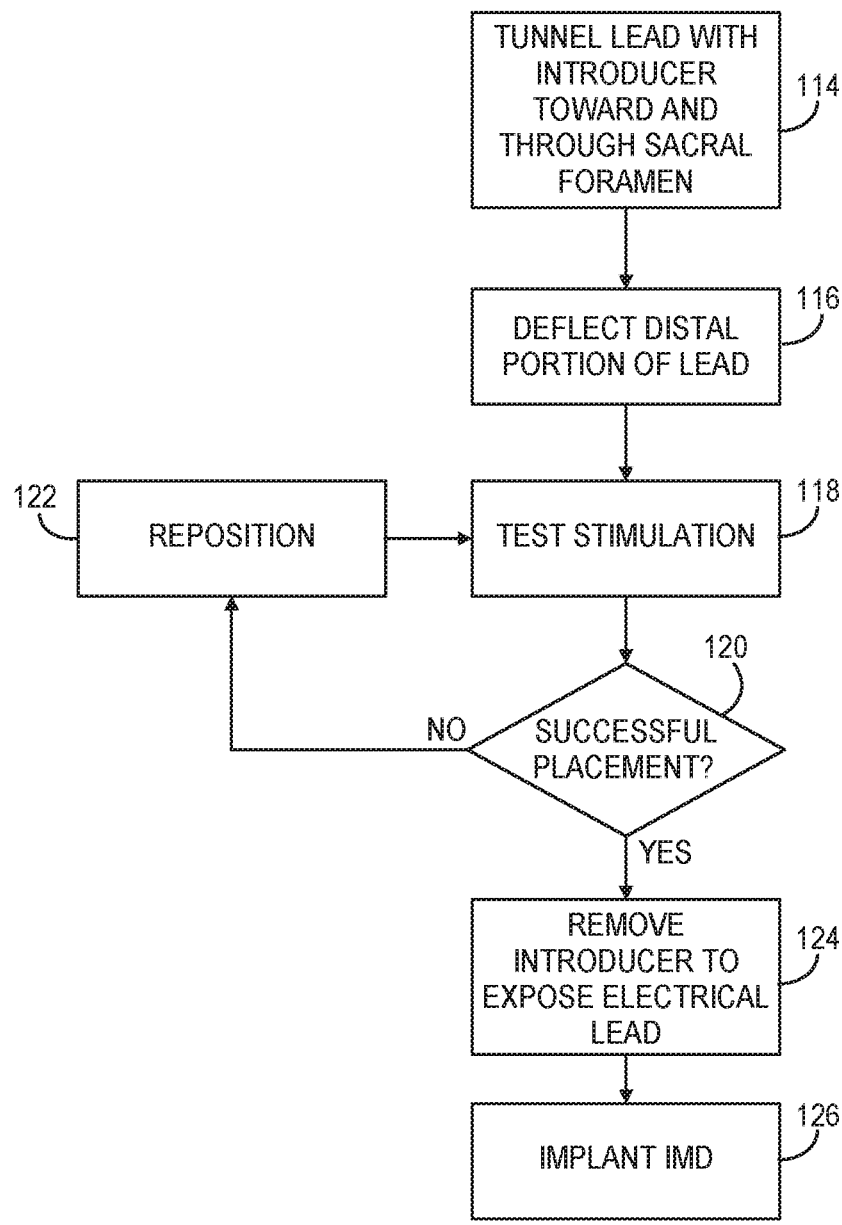
FIG. 17 is a flow chart illustrating an example technique for implanting a lead of an implantable medical device with a deflecting tip adjacent to a sacral nerve.

FIG. 17 is a flow chart illustrating an example technique for implanting an implantable medical device with a deflecting lead tip adjacent to a sacral nerve. FIG. 17 is described with reference to FIG. 1 but may be used for implantation of an implantable medical device in any example described herein and/or with any combination of features described herein.

The technique, or procedure, is described to provide a physician with a simple, effective, and repeatable method for accessing a sacral nerve deep in pelvis 10 of a patient. Using lead 30 of IMD 24, a physician may pierce the skin of a patient's lower back or buttocks and tunnel lead 30 toward and through sacral foramen 20 by using a forward and downward motion (114).

The physician may use the deflection actuator 28 to deflect a distal end of lead 30 to attempt to place the deflected distal end of lead 30 adjacent to the sacral S3 nerve 38 (116).

The physician may perform test stimulation to determine correct placement of lead 30 and capture sacral S3 nerve 38 (118). For example, electrodes on lead 30 exposed by apertures in introducer 31, as described above with reference to FIGS. 4A and 4B, or electrodes within introducer 31, also as described with reference to FIGS. 4A and 4B, may be used to apply test stimulation.

One or more responses to the test stimulation may be measured and/or observed to determine whether placement of the lead 30 is successful (120). For example, muscle movement, sensation indicated by the patient, pain relief, electrical response measured by EMG and/or evoked field response, a bellows response by contraction of the levator ani visibly or otherwise measurably lifting the pelvic floor and/or the anal sphincter, and/or any other suitable response may be used to determine successful stimulation of sacral S3 nerve 38 and successful placement of lead 30 within patient.

If the physician determines, based on the response or lack of response to the test stimulation, that placement of lead 30 is not successful, the physician may reposition lead 30 by, for example, repositioning lead 30 by movement of housing 26 and/or changing the deflection of the distal portion of lead 30 using deflection actuator 28, to attempt to capture sacral S3 nerve 38 (118). After repositioning, physician may repeat the steps of applying test stimulation (118) and determining whether placement is successful (120). The physician may repeat these steps of repositioning (122), applying test stimulation (118), and determining whether placement is successful (120) until the physician determines that placement is successful or decides to remove lead 30 to try a new device and/or an alternative procedure or course of action.

In some examples, the physician may deflect the distal portion of lead (116), apply test stimulation (118), and look for feedback to determine successful position (120) simultaneously.

If the placement of lead 30 is successful, the physician may continue to remove introducer 31 from lead 30 to expose electrical lead 30 (124). In some examples, the physician may also lock deflection actuator 28 in place before removing introducer 31. After removing introducer 31 from lead 30, the physician may implant housing 26 of IMD 24 (126).

In some examples, cylindrical IMD 52 may be used instead of IMD 24. The procedure of FIG. 17 remains similar, with an alternative method in inserting lead 30 and implanting IMD 52. IMD 52 may allow for an improved twisting motion to tunnel the introducer covering lead 30 through sacral foramen 20 and reach sacral S3 nerve 38.

In other examples, the procedure of FIG. 17 may be similar when implanting a lead near a different nerve of the pelvic floor. For example, the procedure may be substantially similar when accessing a different sacral nerve. However, reaching the nerve of a different sacral nerve may require a slightly different deflection of lead 30 to appropriately position a lead adjacent to the nerve.

In addition, any of the described units, devices, or components may be implemented together or separately as discrete but interoperable devices. Depiction of different features as units or components is intended to highlight different functional aspects and does not necessarily imply that such units or components must be realized by separate hardware or software components. Rather, functionality associated with one or more units or components may be performed by separate hardware or software components, or integrated within common or separate hardware or software components.

Although particular dimensions of components have been described, components of any suitable dimensions may be used according to particular needs.

When implemented in software, the functionality ascribed to the techniques, devices, and systems described in this disclosure, such as those described with respect to INS 29A and INS 29B with reference to FIGS. 15 and 16, may be embodied as instructions on a computer-readable medium such as RAM, ROM, NVRAM, EEPROM, FLASH memory, magnetic data storage media, optical data storage media, or the like. The instructions may be executed to support one or more aspects of the functionality described in this disclosure. In some examples, computer-readable storage media may comprise non-transitory media. The term "non-transitory" may indicate that the storage medium is tangible and is not embodied in a carrier wave or a propagated signal. In certain examples, a non-transitory storage medium may store data that can, over time, change (e.g., in RAM or cache).

The program code may be executed by one or more processors, such as processors 104 illustrated and described with reference to FIGS. 15 and 16, which may include one or more DSPs, general purpose microprocessors, ASICs, FPGAs, or other equivalent integrated or discrete logic circuitry. In this sense, the techniques are implemented in hardware, whether implemented entirely in hardware or in hardware such as a processor executing computer-readable code. Accordingly, the term "processor," as used herein may refer to any of the foregoing structure or any other structure suitable for implementation of the techniques described herein.

Various examples have been described. These and other examples are within the scope of the following claims.

The invention claimed is:

1. An implantable medical device comprising:
   an implantable housing;
   a neurostimulator within the housing;
   a plurality of electrodes;
   an implantable lead coupled to the housing, the implantable lead comprising at least one electrode of the plurality of electrodes and one or more conductors coupling the at least one electrode to the neurostimulator;
   an actuator formed with the housing and configured to cause at least a portion of the implantable lead to deflect; and
   a pull-wire connected to a distal portion of the implantable lead and connected to the actuator, wherein the actuator is configured such that movement of the actuator in a first direction increases tension on the pull-wire to cause the deflection of the at least a portion of the lead.

2. The implantable medical device of claim 1, wherein the neurostimulator is configured to deliver electrical stimulation to the implantable lead to provide stimulation therapy to at least one nerve.

3. The implantable medical device of claim 1, wherein the actuator is configured to cause the implantable lead to deflect from a first shape to a second shape, wherein the second shape comprises a curve of a radius R in a range of approximately 1 mm to 40 mm.

4. The implantable medical device of claim 3, wherein the radius R is in a range of approximately 1.5 mm to 25 mm.

5. The implantable medical device of claim 1, wherein the implantable housing has:
   a length in a range of approximately 10 mm to 30 mm;
   a width in a range of approximately 0.5 mm to 10 mm; and
   a thickness in a range of approximately 0.5 mm to 5 mm.

6. The implantable medical device of claim 5, wherein:
   the length is in a range of approximately 10 mm to 15 mm;
   the width is in a range of approximately 2 mm to 4 mm; and
   the thickness is in a range of approximately 1 mm to 3 mm.

7. The implantable medical device of claim 1, wherein:
   the implantable lead, when deflected, includes a first portion and a second portion, the first portion being not substantially deflected and extending substantially along a first axis and the second portion being substantially deflected and extending substantially along a second axis;
   the first axis and the second axis form an angle; and
   the angle is in a range of approximately 10 degrees to 60 degrees.

8. The implantable medical device of claim 7, wherein the angle is in a range of approximately 35 degrees to 50 degrees.

9. The implantable medical device of claim 1, wherein:
   the implantable lead, when deflected, includes a first portion and a second portion, the first portion being not substantially deflected and extending substantially along a first axis and the second portion being substantially deflected and extending substantially along a second axis, and
   the second portion has a length in a range of approximately 5 mm to 40 mm.

10. The implantable medical device of claim 1, further comprising power circuitry within the implantable housing, wherein the power circuitry is configured to:
    deliver power to the neurostimulator; and
    be charged by an external programmer.

11. The implantable medical device of claim 1, further comprising a power source, wherein the power source is configured to deliver power to the neurostimulator.

12. The implantable medical device of claim 1, wherein:
    the housing comprises external threads; and
    the actuator comprises:
      a knob with internal threads configured to engage with at least a portion of the external threads, and
      a pull ring connected to the pull-wire,
    wherein rotation of the knob results in translation of the pull ring and translation of the pull-wire with respect to the lead, increasing tension on the pull-wire and causing deflection of the lead.

13. The implantable medical device of claim 1, further comprising a ratchet system for ratcheting the pull-wire.

14. The implantable medical device of claim 1, wherein the actuator is configured to be actuated by translation of at least a portion of the actuator.

15. The implantable medical device of claim 14, wherein the actuator comprises a locking mechanism configured to lock in place the deflection of the implantable lead.

16. The implantable medical device of claim 15, wherein at least a portion of the actuator may be rotated to lock in place the deflection of the implantable lead.

17. The implantable medical device of claim 1, wherein the actuator is configured to be actuated by rotation of at least a portion of the actuator.

18. The implantable medical device of claim 1, wherein the actuator is configured to cause the implantable lead to deflect a distance in the range of approximately 0.1 mm to 20 mm.

19. A method of positioning an implantable medical device within a patient, the implantable medical device comprising an implantable housing, a neurostimulator within the housing, a plurality of electrodes, an implantable lead coupled to the housing, the implantable lead comprising at least one electrode of the plurality of electrodes and one or more conductors coupling the at least one electrode to the neurostimulator, and a pull-wire connected to a distal portion of the implantable lead and connected to an actuator formed at least partially within the housing, wherein the actuator is configured such that movement of the actuator in a first direction increases tension on the pull-wire to cause deflection of at least a portion of the implantable lead, and the method comprising deflecting the at least a portion of the implantable lead in response to movement of the actuator.

20. The method of claim 19, further comprising delivering electrical stimulation, by the neurostimulator, to the implantable lead to provide stimulation therapy to at least one nerve.

21. The method of claim 19, wherein deflecting at least a portion of the implantable lead in response to movement of the actuator comprises deflecting the implantable lead from a first shape to a second shape, wherein the second shape comprises a curve of a radius R in a range of approximately 1 mm to 40 mm.

22. The method of claim 21, wherein the radius R is in a range of approximately 1.5 mm to 25 mm.

23. The method of claim 19, wherein:
    the implantable lead, when deflected, includes a first portion and a second portion, the first portion being not substantially deflected and extending substantially along a first axis and the second portion being substantially deflected and extending substantially along a second axis; the first axis and the second axis form an angle; and
    the angle is in a range of approximately 10 degrees to 60 degrees.

24. The method of claim 23, wherein the angle is in a range of approximately 35 degrees to 50 degrees.

25. The method of claim 19, wherein:
    the implantable lead, when deflected, includes a first portion and a second portion, the first portion being not substantially deflected and extending substantially along a first axis and the second portion being substantially deflected and extending substantially along a second axis, and
    the second portion has a length in a range of approximately 5 mm to 40 mm.

26. The method of claim 19, wherein the implantable medical device further comprises power circuitry within the implantable housing, wherein the method further comprises:
    receiving charge, by the power circuitry, from an external programmer; and
    delivering power, by the power circuitry, to the neuro stimulator.

27. The method of claim 19, further comprising a power source, wherein the method further comprises delivering power, by the power source, to the neurostimulator.

28. The method of claim 19, wherein deflecting at least the portion of the implantable lead in response to movement of the actuator comprises deflecting the portion a distance in the range of approximately 0.1 mm to 20 mm.

* * * * *